US012422736B2

(12) United States Patent
Houjou et al.

(10) Patent No.: US 12,422,736 B2
(45) Date of Patent: Sep. 23, 2025

(54) IMAGING DEVICE COVER, IMAGING DEVICE, AND IMAGING METHOD

(71) Applicant: CASIO COMPUTER CO., LTD., Tokyo (JP)

(72) Inventors: Yoshiharu Houjou, Tokyo (JP); Tohru Yoshida, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 214 days.

(21) Appl. No.: 18/024,887

(22) PCT Filed: Aug. 20, 2021

(86) PCT No.: PCT/JP2021/030580
§ 371 (c)(1),
(2) Date: Mar. 6, 2023

(87) PCT Pub. No.: WO2022/050084
PCT Pub. Date: Mar. 10, 2022

(65) Prior Publication Data
US 2023/0314915 A1  Oct. 5, 2023

(30) Foreign Application Priority Data
Sep. 7, 2020  (JP) .................. 2020-149989
Jan. 26, 2021  (JP) .................. 2021-010405

(51) Int. Cl.
*G03B 17/56* (2021.01)
*A61B 5/00* (2006.01)

(52) U.S. Cl.
CPC ............ *G03B 17/56* (2013.01); *A61B 5/0077* (2013.01); *A61B 5/445* (2013.01); *A61B 2562/146* (2013.01); *A61B 2562/185* (2013.01)

(58) Field of Classification Search
None
See application file for complete search history.

(56) References Cited

U.S. PATENT DOCUMENTS

2021/0092268 A1*  3/2021  Lin .................... G02B 13/0015

FOREIGN PATENT DOCUMENTS

| CN | 105125170 A | * 12/2015 | ............ A61B 46/10 |
| JP | H07255704 A | 10/1995 | |
| JP | 2016214552 A | 12/2016 | |
| JP | 2018163240 A | 10/2018 | |
| JP | 3225158 U | 2/2020 | |

(Continued)

OTHER PUBLICATIONS

First Examination Opinion Notification dated Feb. 22, 2023 received in Taiwanese Patent Application No. TW 110132779.

(Continued)

*Primary Examiner* — Rodney E Fuller
(74) *Attorney, Agent, or Firm* — Scully, Scott, Murphy & Presser, P.C.

(57) ABSTRACT

An imaging device cover includes a cover member including at least a partial region that transmits incident light, and a first adhesive layer provided on a cover peripheral portion that is a peripheral portion of the cover member. While covering an object cover that guides reflected light from a target to a lens of an imaging device, the cover member is peelably attached to the imaging device including the object cover via the first adhesive layer.

24 Claims, 35 Drawing Sheets

(56) References Cited

FOREIGN PATENT DOCUMENTS

| KR | 20080107869 A | 12/2008 | | |
|---|---|---|---|---|
| KR | 20150066790 A | 6/2015 | | |
| WO | 2004111720 A1 | 12/2004 | | |
| WO | 2008116140 A2 | 9/2008 | | |
| WO | WO-2009051756 A1 * | 4/2009 | ............. | G03B 11/00 |
| WO | WO-2018148668 A1 * | 8/2018 | ............... | G02B 1/18 |
| WO | 2018219857 A1 | 12/2018 | | |

OTHER PUBLICATIONS

Extended European Search Report dated Feb. 7, 2024 received in European Patent Application No. EP 21864142.1.
International Search Report dated Oct. 26, 2021 issued in PCT/JP2021/030580.

* cited by examiner

IMAGING DEVICE COVER, IMAGING DEVICE, AND IMAGING METHOD

TECHNICAL FIELD

The present disclosure relates to an imaging device cover, an imaging device, and an imaging method.

BACKGROUND ART

Various inspection devices for non-invasive inspection of a human body have been put into practical use. For example, Patent Literature 1 discloses a dermoscopy camera that captures an image for supporting diagnosis of a diseased area by capturing the image while an adapter is brought into contact with a skin. Since such a dermoscopy camera is used with a part of the camera in contact with a patient's skin, sanitation needs to be taken into consideration when the camera is used for different patients. This leads to capturing an image by attaching a peelable transparent sheet to a part that comes into contact with the patient's skin, specifically, a transparent object cover of the dermoscopy camera, and to capturing an image by replacing the transparent sheet for each patient to be captured.

CITATION LIST

Patent Literature

Patent Literature 1: Unexamined Japanese Patent Application Publication No. 2016-214552

SUMMARY OF INVENTION

Technical Problem

However, in such a case, when an adhesive layer provided on the transparent sheet is provided to cover the entire object cover, the quality of a captured image may be degraded due to an influence of the adhesive layer. Furthermore, when a part of the adhesive layer remains on the object cover, particularly, a central part of the object cover when the transparent sheet is peeled off, the quality of a captured image may be further degraded because the transparent sheet is attached to the remaining adhesive layer.

The present disclosure has been made to solve the above problems, and an objective of the present disclosure is to provide to an imaging device cover, an imaging device, and an imaging method, capable of capturing an appropriate image while taking into consideration the sanitation of the imaging device.

Solution to Problem

In order to achieve the above objective, an imaging device cover of the present disclosure includes a cover member comprising at least a partial region that transmits incident light, and a first adhesive layer provided on a cover peripheral portion that is a peripheral portion of the cover member. While covering an object cover that guides reflected light from a target to a lens of an imaging device, the cover member is peelably attached to the imaging device including the object cover via the first adhesive layer.

Advantageous Effects of Invention

According to the present disclosure, an appropriate image can be captured while taking into consideration the sanitation of an imaging device.

DESCRIPTION OF EMBODIMENTS

Hereinafter, an imaging device cover, an imaging device, and an imaging method according to embodiments of the present disclosure are described with reference to the drawings.

Embodiment 1

Figure 1:
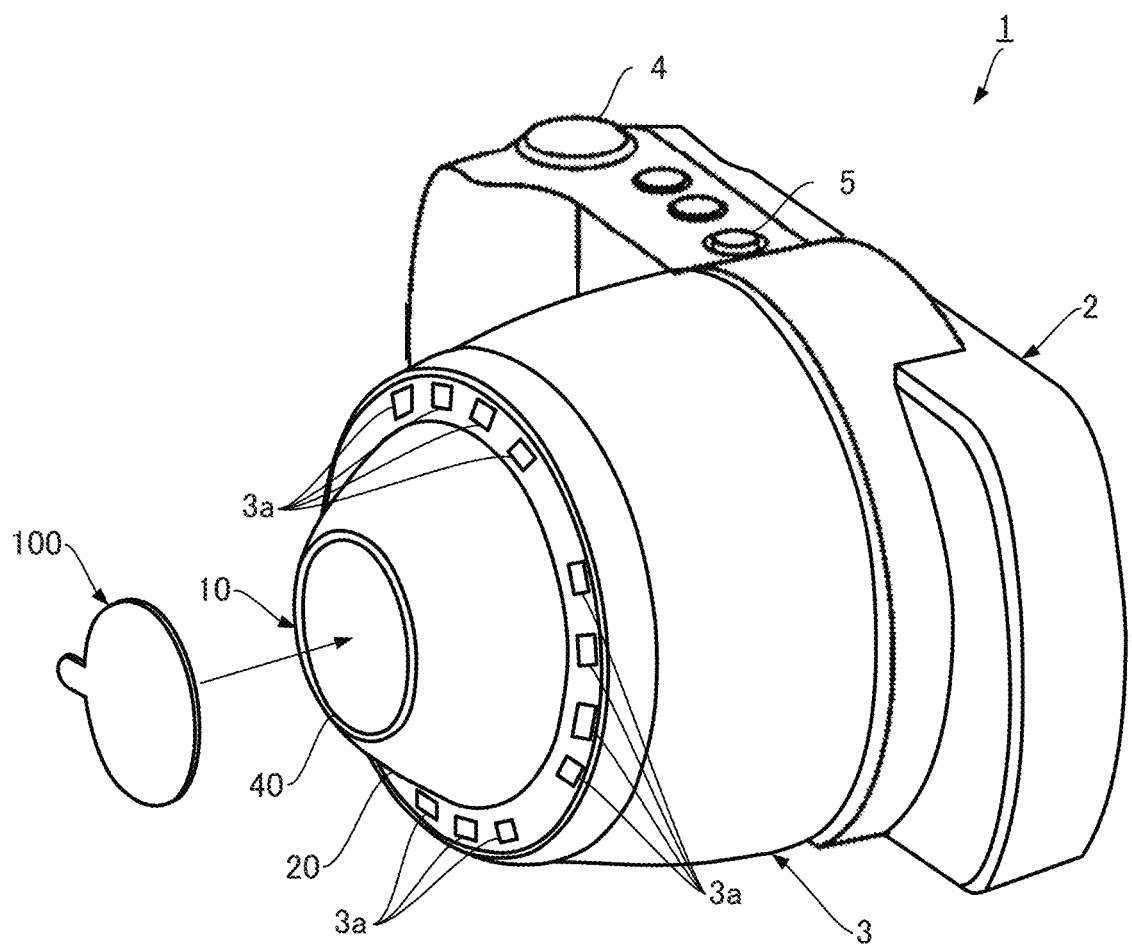
FIG. 1 is a perspective view of an imaging device and an imaging device cover according to Embodiment 1 of the present disclosure.

As illustrated in FIG. 1, an imaging device 1 is, for example, a dermoscopy camera that captures an image for examining the condition of a skin that is a subject. The imaging device 1 includes a controller 2 and a camera body 3 provided in front of the controller 2. An imaging device cover 100 is attached to the imaging device 1 at the time of imaging, and covers an object cover 40 at a distal end of a cover structure 10.

The controller 2 is provided with a touch panel type liquid crystal monitor 6 (FIG. 2) and operation buttons such as a shutter button 4 and a power button 5.

Figure 2:
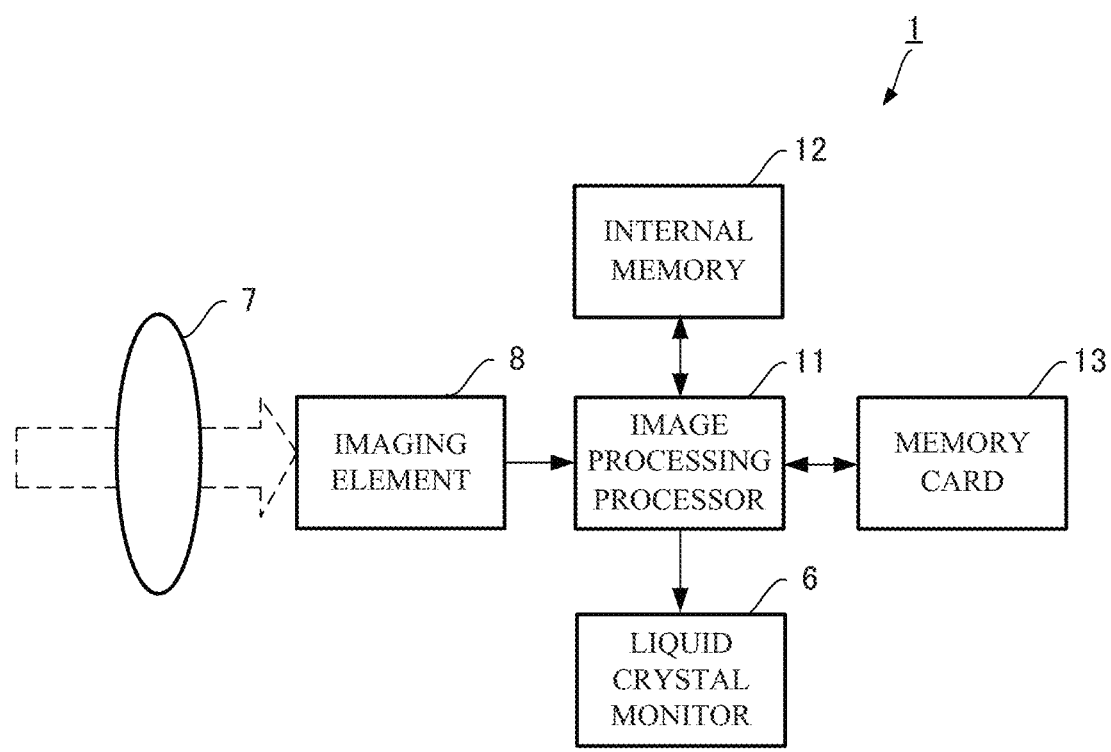
FIG. 2 is a block diagram schematically illustrating the internal configuration of the imaging device according to Embodiment 1 of the present disclosure.

As illustrated in FIG. 2, the camera body 3 includes an imaging lens system 7, an imaging element 8, and a plurality of light emitting diodes (LEDs) as light sources. The imaging element 8 is configured to be able to convert light in a convertible wavelength region including a wavelength range of visible light into an electrical signal. The plurality of LEDs includes LEDs that emit light when a skin disease area is captured using the imaging device 1 as a general camera (normal imaging), and LEDs that emit light when performing dermoscopy imaging. The camera body 3 is provided with an image processing processor 11 and an internal memory 12. The image processing processor 11 includes a central processing unit (CPU) as a processor. The image processing processor 11 executes a program stored in the internal memory 12 such as a flash memory or a read only memory (ROM) and controls the camera body 3. The image processing processor 11 generates an image signal by performing various necessary processes such as level conversion on the electrical signal transmitted from the imaging element 8. The image processing processor 11 transmits overflow data during image processing and processed data to the internal memory 12, and retrieves the processed data from the internal memory 12 when the image processing ends. The image processing processor 11 records produced image data in a memory card 13. Furthermore, the image processing processor 11 outputs the image data to the liquid crystal monitor 6, and displays an image on the liquid crystal monitor 6 by a driver (not illustrated). The liquid crystal monitor 6 serves as a viewfinder and displays an image for determining composition before imaging. Note that the image processing processor 11 may have a multiprocessor configuration including a plurality of processors. The image processing processor 11 may be configured by a combination of a CPU and other electric circuits.

Figure 3:
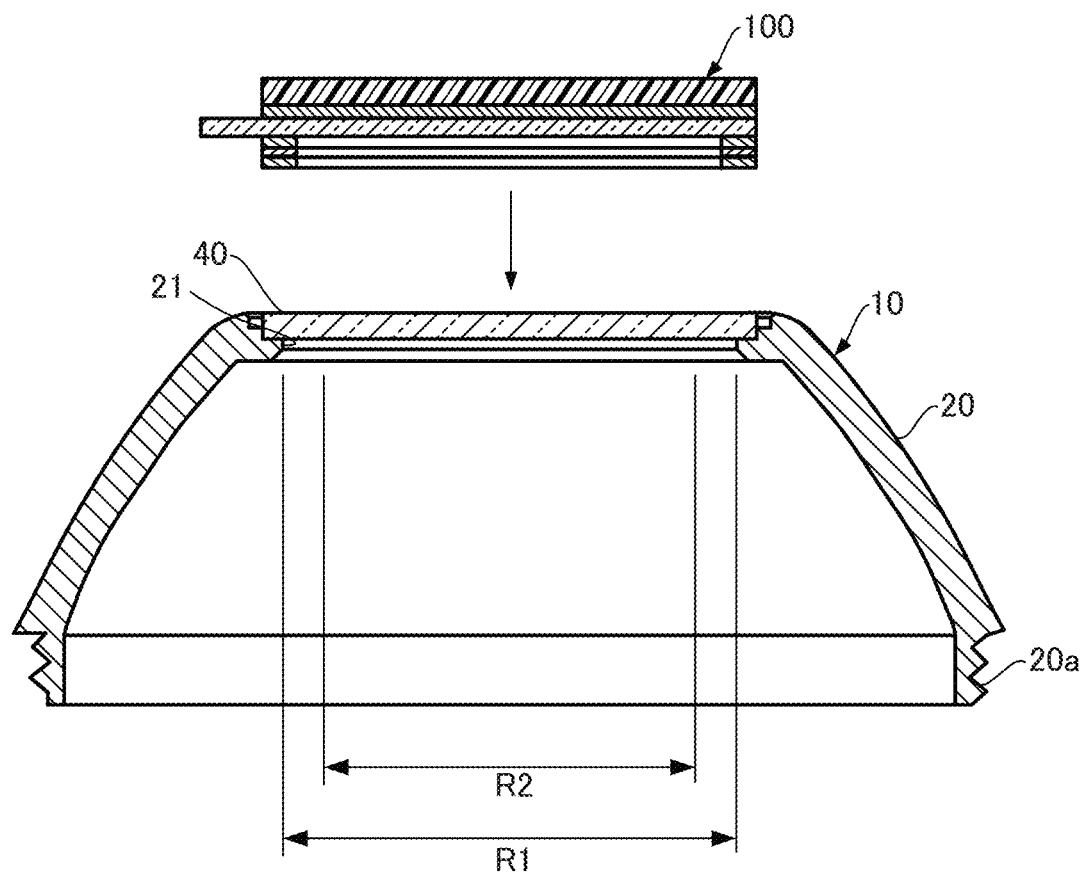
FIG. 3 is a cross-sectional view of the imaging device cover and a cover structure according to Embodiment 1 of the present disclosure.

As illustrated in FIG. 1, the camera body 3 includes the cover structure 10 provided on the subject side. As illustrated in FIGS. 1 and 3, the cover structure 10 includes a support 20 formed in a truncated cone tubular shape and the object cover 40 attached to close an opening 21 (FIG. 3) formed at the top (front end) of the support 20 and supported by the support 20. The support 20 is made of a material that does not transmit light so that transmitted light is not converted into an electric signal by the imaging device 8 (FIG. 2), and is made of, for example, a polyvinyl chloride derivative or resin such as acrylic resin. A surface of the support 20 may be coated with paint for preventing transmission of light. An inner peripheral surface of the support 20 is subjected to texturing or antireflection coating to suppress reflection of light. Note that a male thread 20a is formed at the bottom (rear end) of the support 20 as illustrated in FIG. 3. The male thread 20a serves as attaching/detaching means for attaching/detaching the cover structure 10 to/from the camera body 3. The object cover 40 includes a light-transmissive member such as a glass cover, and is formed in a disc shape. When an image is captured using the imaging device 1, the imaging device cover 100 is attached and the front surface of the object cover 40 is covered with the imaging device cover 100.

When dermoscopy imaging of a skin disease area is performed (second imaging state), suppressing irregular reflection of light on the skin surface is important. In order to suppress the irregular reflection of light, gel is applied to the skin disease area, and the object cover 40 is pressed against the skin disease area via the imaging device cover 100. Thus, an air layer between the skin disease area and the object cover 40 is blocked, so that the irregular reflection of light on the skin surface can be suppressed. In this way, the imaging device cover 100 and the object cover 40 pressed against the skin disease part transmit light from the above-described LEDs (not illustrated) provided inside the camera body 3, thereby allowing the skin disease area to be irradiated with the light. Furthermore, the imaging device cover 100 and the object cover 40 allow light reflected by the skin disease area to enter the imaging device 1 and guide the light to the above-described imaging lens system 7 (FIG. 2) provided inside the camera body 3, and the imaging element 8 (FIG. 2) receives the light from the imaging lens system 7 (FIG. 2). This enables dermoscopy imaging.

When the skin disease area is captured by normal imaging (first imaging state), light is emitted from a plurality of light exit holes 3a formed around the cover structure 10 illustrated in FIG. 1 and the skin disease area is irradiated with the light in a state in which the imaging device cover 100 and the object cover 40 are separated from the skin disease area. The imaging device cover 100 and the object cover 40 allow light reflected by the skin disease area to enter the imaging device 1 and guide the light to the above-described imaging lens system 7 (FIG. 2) provided inside the camera body 3, and the imaging element 8 (FIG. 2) receives the light from the imaging lens system 7 (FIG. 2). This enables normal imaging. In this way, the imaging device 1 performs the dermoscopy imaging and the normal imaging to capture an image for supporting diagnosis of the skin disease area.

Figure 4:
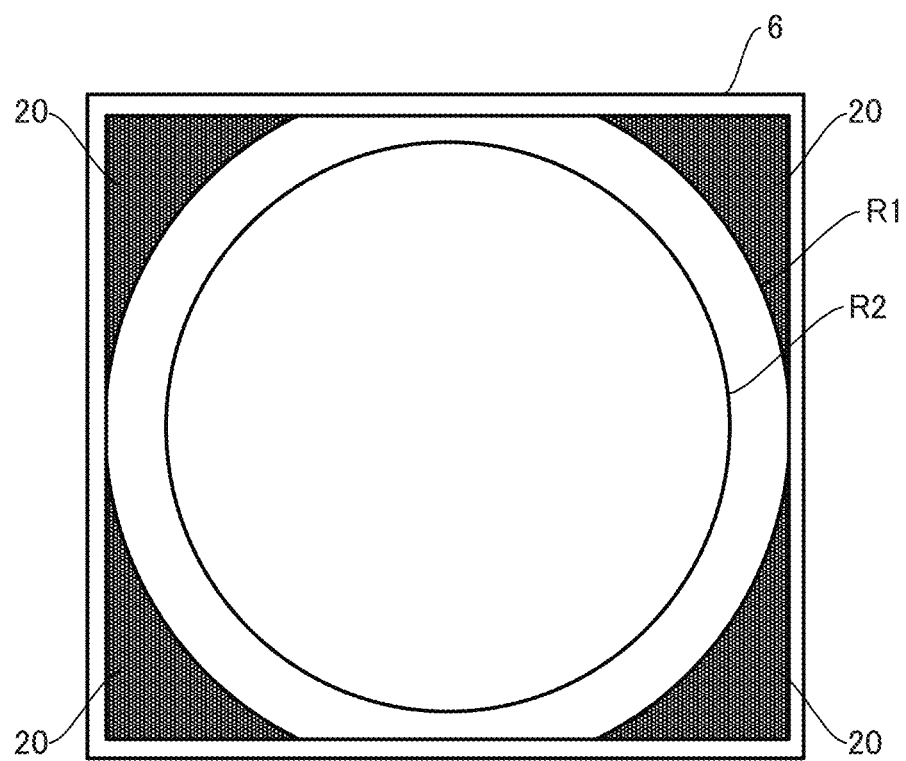
FIG. 4 is an explanatory view of an image projected on a liquid crystal monitor of the imaging device according to Embodiment 1 of the present disclosure at the time of imaging.

As described above, since the support 20 is made of a material that does not transmit light, the support 20 is projected darkly (black) on the liquid crystal monitor 6 at the time of imaging as illustrated in FIG. 4. In FIG. 4, the support 20 that is projected darkly on the liquid crystal monitor 6 is hatched. On the other hand, as illustrated in FIG. 3, the opening 21 formed in the support 20 is a region that can be captured by light incident through the object cover 40. Therefore, the region where the opening 21 is formed is defined as a capturable region R1 as a region that can be captured by the imaging device 1. As illustrated in FIG. 4, the capturable region R1 is projected brightly in the center of the liquid crystal monitor 6 at the time of imaging. As illustrated in FIG. 3, within the capturable region R1, a capturing assurance region R2 is defined as a region where an optically appropriate image can be captured with little distortion in the captured image. The skin disease area to be imaged is recommended to be captured within the capturing assurance region R2. Therefore, the liquid crystal monitor 6 that displays an image as a viewfinder displays a circle indicating the capturing assurance region R2. As illustrated in FIG. 4, the capturing assurance region R2 is a circular region smaller than the capturable region R1, and has a center matching the center of the capturable region R1.

Figure 5:
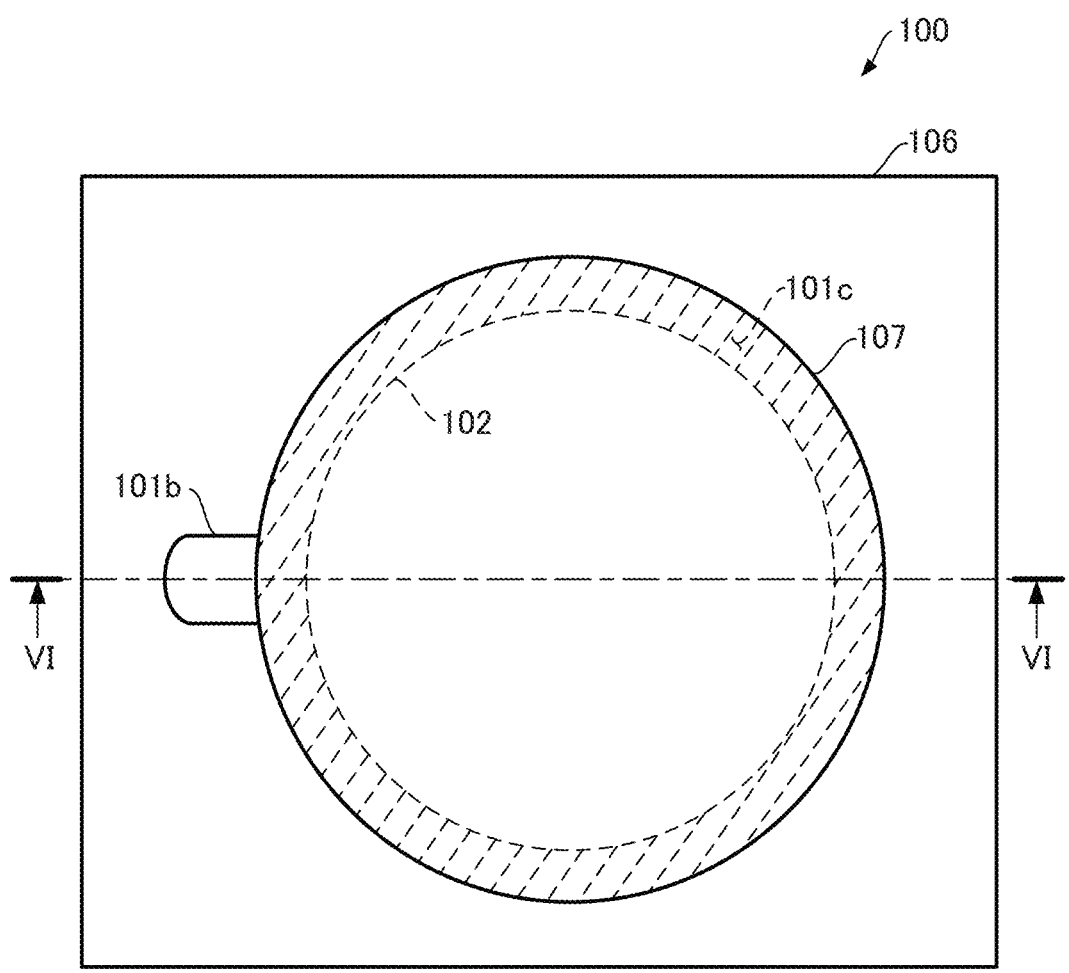
FIG. 5 is a plan view of the imaging device cover according to Embodiment 1 of the present disclosure.
Figure 6:
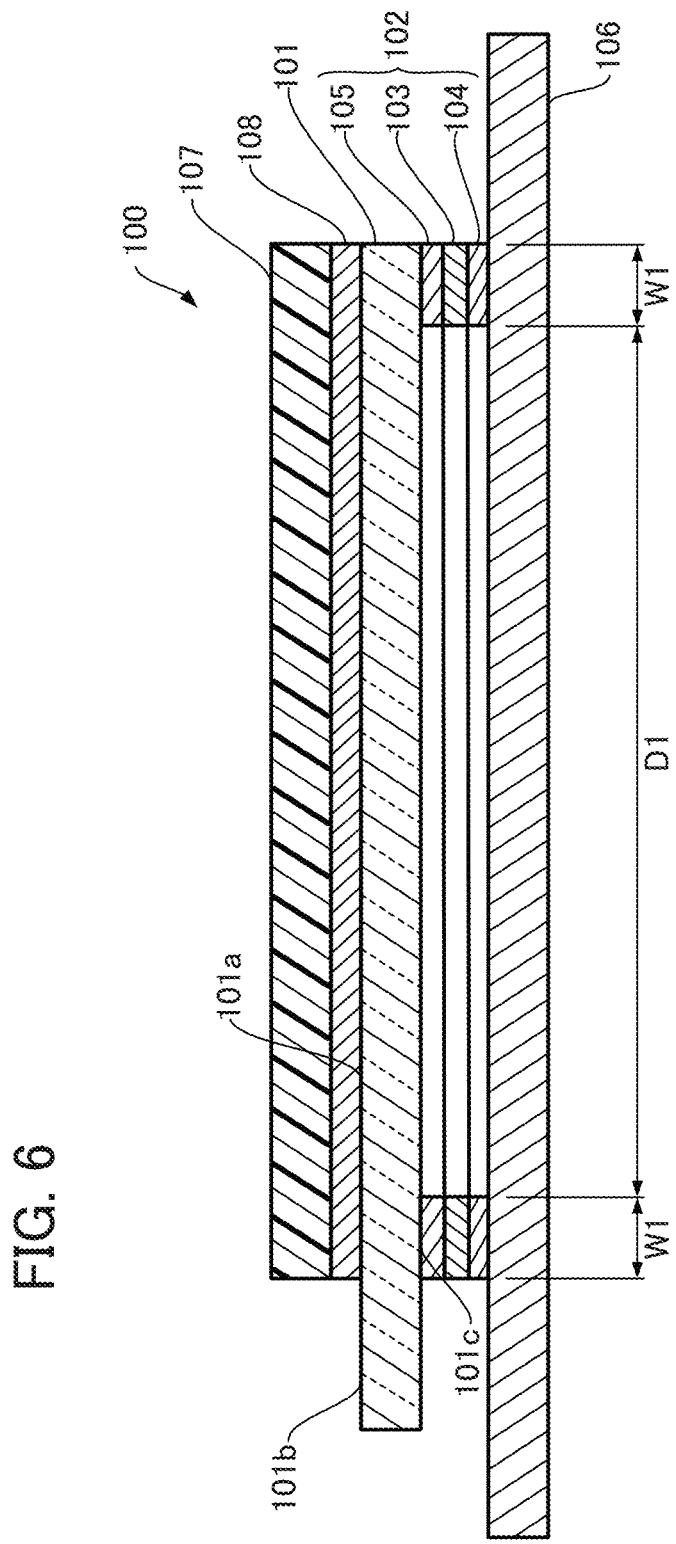
FIG. 6 is a cross-sectional view of the imaging device cover viewed from the cross-sectional line VI-VI in FIG. 5.

As illustrated in FIG. 6, the imaging device cover 100 includes a cover member 101 made of a transparent sheet material, a double-sided tape 102 attached to one surface of the cover member 101, and a base sheet 106 attached to the cover member 101 via the double-sided tape 102, and a protective member 107 attached to the other surface of the cover member 101 via a third adhesive layer 108. Note that the double-sided tape 102 is provided on a cover peripheral portion 101c that is the peripheral portion of the cover member 101. In FIG. 5, the double-sided tape 102 covered with the cover member 101, the third adhesive layer 108, and/or the like is hatched so that the shape of the double-sided tape 102 can be easily understood. Consequently, the hatching does not represent the cross section of a member. The cover peripheral portion 101c is also hatched. In the cross-sectional view of the imaging device cover 100 illustrated in FIG. 6, the thickness of each component is shown thicker than the actual thickness so that the configuration can be understood. This also applies to the cross-sectional views of the imaging device cover 100 in FIG. 6 and subsequent drawings.

The cover member 101 is made of, for example, a transparent polycarbonate sheet material having a thickness of 188 μm. The cover member 101 includes a circular portion 101a having a diameter approximately equal to the diameter of the object cover 40 illustrated in FIGS. 1 and 3, and a protruding portion 101b protruding outward from an outer edge of the circular portion 101a. The protruding portion 101b is a portion to be held by an object person (user) when attaching or detaching the imaging device cover 100.

The double-sided tape 102 includes a colored layer 103 as a base material, a first adhesive layer 104 made of a repeelable acrylic adhesive, and a second adhesive layer 105 made of an acrylic adhesive having a higher adhesive strength than the first adhesive layer 104. The colored layer 103 is, for example, polyester colored black and having a thickness of 16 μm. The second adhesive layer 105 having a high adhesive strength is provided on one surface of the colored layer 103. The colored layer 103 is strongly attached to the cover member 101 via the second adhesive layer 105. On the other hand, the other surface of the colored layer 103 is provided with the first adhesive layer 104 having a lower adhesive strength than the second adhesive layer 105. The colored layer 103 is peelably attached to the base sheet 106 via the first adhesive layer 104.

As illustrated in FIG. 5, the double-sided tape 102 has an annular planar shape with a circular hole provided in the center thereof, and has an outer diameter the same as the outer diameter of the circular portion 101a (FIG. 6) of the cover member 101. The double-sided tape 102 is attached with its center matching the center of the cover member 101. Thus, an outer edge of the double-sided tape 102 matches the outer edge of the cover member 101. As illustrated in FIG. 6, a width W1 of the double-sided tape 102 affects the adhesive strength of the double-sided tape 102. The double-sided tape 102 needs to have an adhesive strength that prevents the imaging device cover 100 from being peeled off from the imaging device 1 at the time of imaging, and needs to have an adhesive strength that allows the imaging device cover 100 to be easily peeled off when the imaging device cover 100 is replaced. The width W1 of the double-sided tape 102 is set to satisfy these two conditions, and is set to 1.5 mm, for example. An inner diameter D1 of the double-sided tape 102 is set to a value smaller than the diameter of the capturable region R1 illustrated in FIG. 3 and to a value larger than the diameter of the capturing assurance region R2.

The base sheet 106 is for preventing dirt, dust, and/or the like from adhering to the first adhesive layer 104. The imaging device cover 100 is stored with the base sheet 106 attached when not in use. The base sheet 106 is made of, for example, a polyethylene sheet material having a thickness of 75 μm and is formed in a rectangular shape. As illustrated in FIG. 6, the cover member 101 is attached to the base sheet 106 via the double-faced tape 102 provided on the peripheral portion of the cover member 101, but the double-faced tape 102 is not attached to the protruding portion 101b of the cover member 101. Therefore, the object person can easily hold, with his/her fingers, the protruding portion 101b not attached to the base sheet 106.

The protective member 107 is made of a light-transmissive material such as a polyethylene sheet material having a thickness of 70 μm, and is formed in a circular shape. The protective member 107 has the same diameter as the cover member 101, and covers and protects the cover member 101 until the cover member 101 is removed at the time of imaging. Note that the protective member 107 is made of a material having lower transmittance and light transmittance than the cover member 101, or is processed to be such a member. Furthermore, the protective member 107 is colored with a bright color, for example, pale green.

The third adhesive layer 108 is coated on one surface of the protective member 107 and attaches the protective member 107 to the cover member 101 in a peelable manner. The third adhesive layer 108 is, for example, a silicone-based adhesive, and is selected from biocompatible adhesives that hardly remain on the cover member 101 when the protective member 107 is peeled off.

Figure 9:
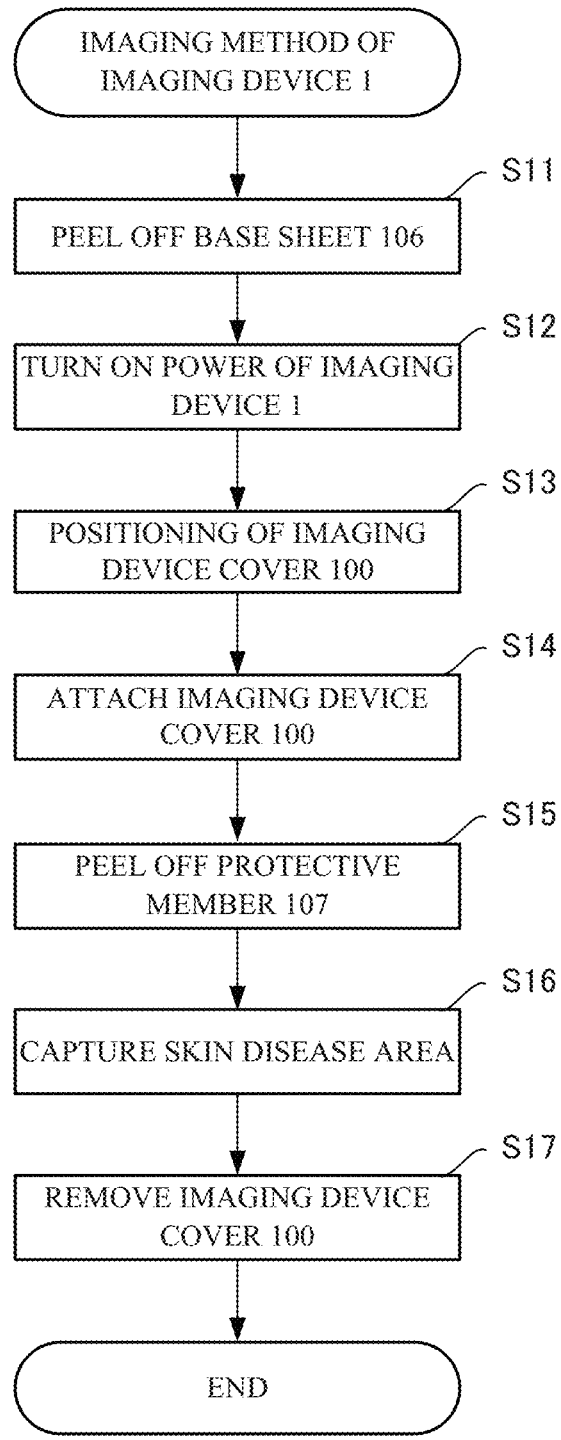
FIG. 9 is a flowchart illustrating an imaging method of the imaging device according to Embodiment 1 of the present disclosure.

Next, an imaging method of the imaging device 1 using the imaging device cover 100 is described. First, as illustrated in FIG. 9, the object person peels off the base sheet 106 from the imaging device cover 100 (step S11). The object person can peel off the first adhesive layer 104 having a low adhesive strength from the base sheet 106 by holding the protruding portion 101b illustrated in FIG. 6 with his/her fingers and separating the first adhesive layer 104 from the base sheet 106.

Subsequently, the object person turns on the power button 5 of the imaging device 1 illustrated in FIG. 1 (step S12). Thus, an image acquired via the imaging element 8 (FIG. 2) is displayed on the liquid crystal monitor 6 (FIG. 8A).

Figure 7A:
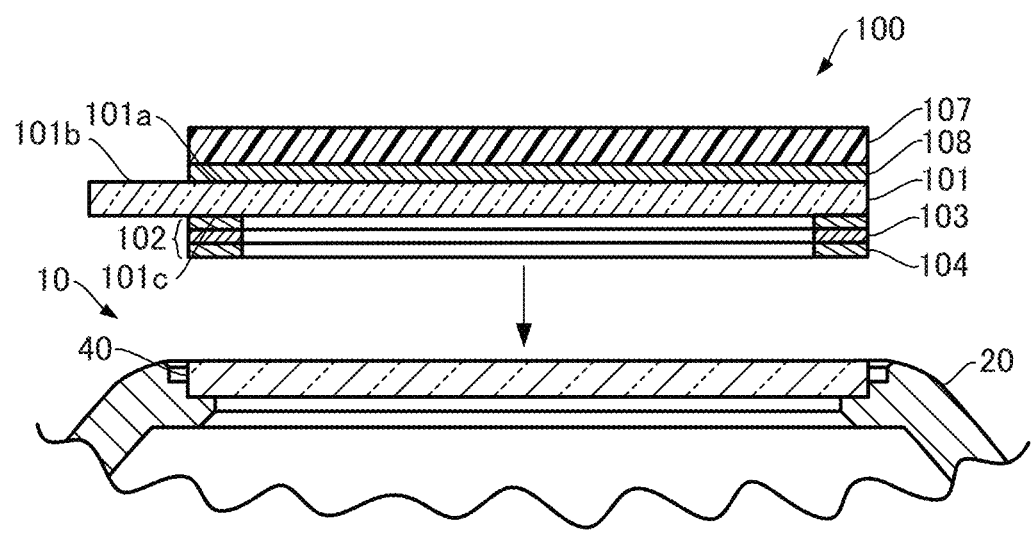
FIG. 7A is a schematic view illustrating how the imaging device cover according to Embodiment 1 of the present disclosure is attached to the imaging device in order of steps.

Subsequently, in order to attach the imaging device cover 100 to the normal attachment position, the object person performs positioning of the imaging device cover 100 (step S13). Specifically, the object person brings the imaging device cover 100 closer to the cover structure 10 as illustrated in FIG. 7A while checking the image displayed on the liquid crystal monitor 6.

Figure 8A:
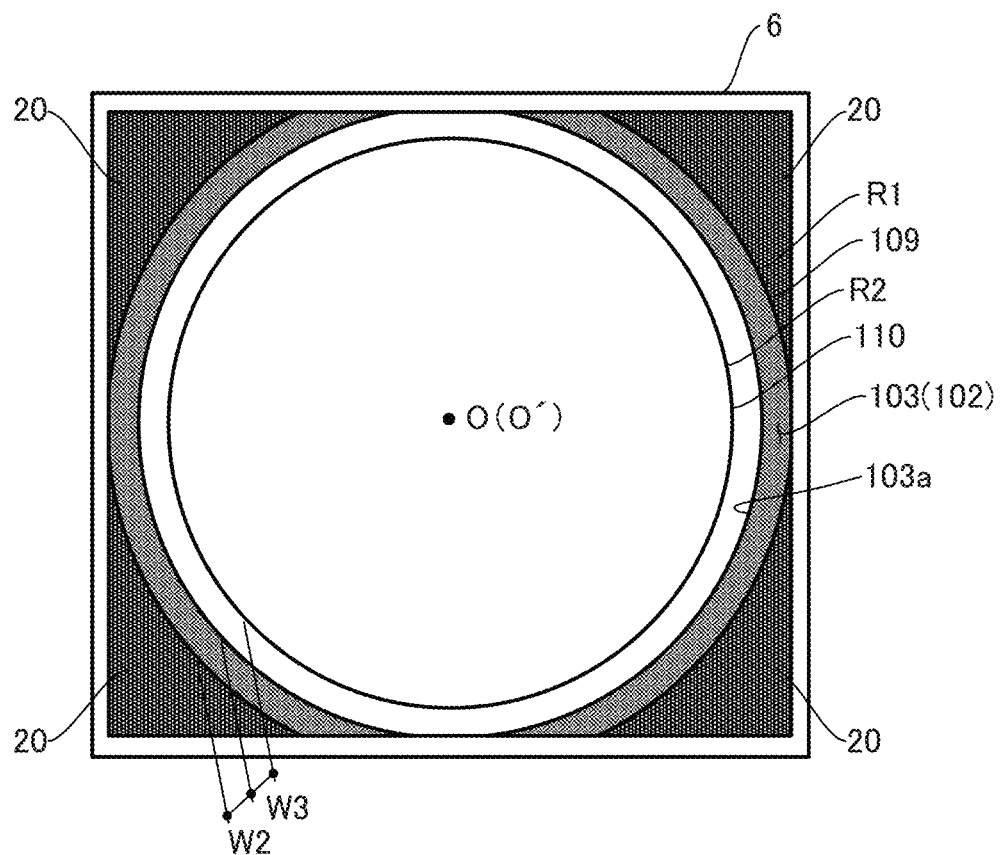
FIG. 8A is an explanatory diagram of an image projected on the liquid crystal monitor when the imaging device cover according to Embodiment 1 of the present disclosure is attached to the imaging device, and is a diagram when the imaging device cover is attached to a normal attachment position.

The normal attachment position of the imaging device cover 100 is a position where the center O of the colored layer 103 (double-sided tape 102) formed in an annular shape (center O is also the center of the circular portion 101a of the cover member 101) matches the center O' of the capturable region R1 (center O' is also the center of the capturing assurance region R2) as illustrated in FIG. 8A. The object person performs the positioning of the imaging device cover 100 to the normal attachment position while viewing the image projected on the liquid crystal monitor 6 illustrated in FIGS. 8A and 8B. Assuming that the imaging device cover 100 is attached to the normal attachment position, a width W2 of the colored layer 103 protruding inward from an outer edge 109 of the capturable region R1 is constant over the entire circumference of the outer edge 109 of the capturable region R1 as illustrated in FIG. 8A. Therefore, whether the imaging device cover 100 is in the normal attachment position or is shifted from the normal attachment position can be intuitively determined by viewing the image on the liquid crystal monitor 6. The object person performs the positioning of the imaging device cover 100 while checking the image on the liquid crystal monitor 6 so that the amount of protrusion from the outer edge 109 of the capturable region R1 to the inside of the colored layer 103 is constant.

Figure 7B:
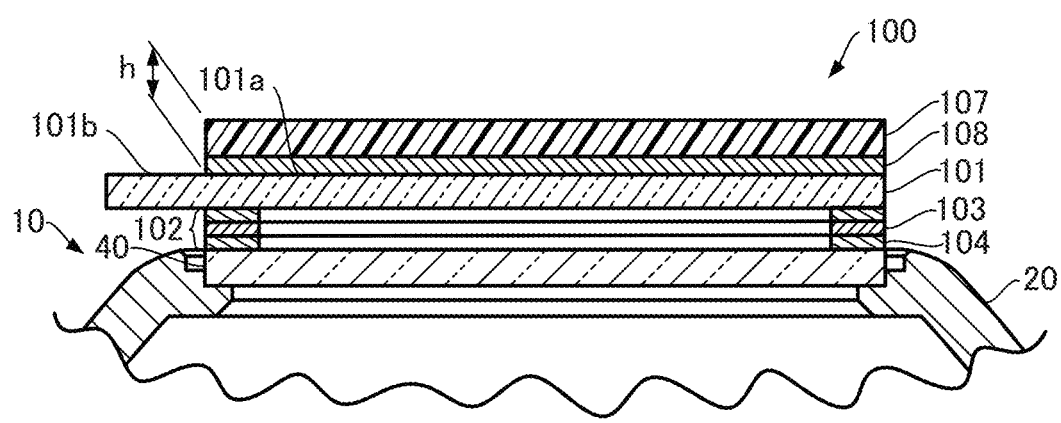
FIG. 7B is a schematic view illustrating how the imaging device cover according to Embodiment 1 of the present disclosure is attached to the imaging device in order of steps.

After performing the appropriate positioning at step S13, the object person attaches the imaging device cover 100 to the imaging cover 1 (step S14). As illustrated in FIG. 7B, the imaging device cover 100 attaches the first adhesive layer 104 so that the outer edge of the first adhesive layer 104 matches the outer edge of the object cover 40. Thus, a surface of the object cover 40 facing a skin disease area can be covered with the imaging device cover 100.

Figure 7C:
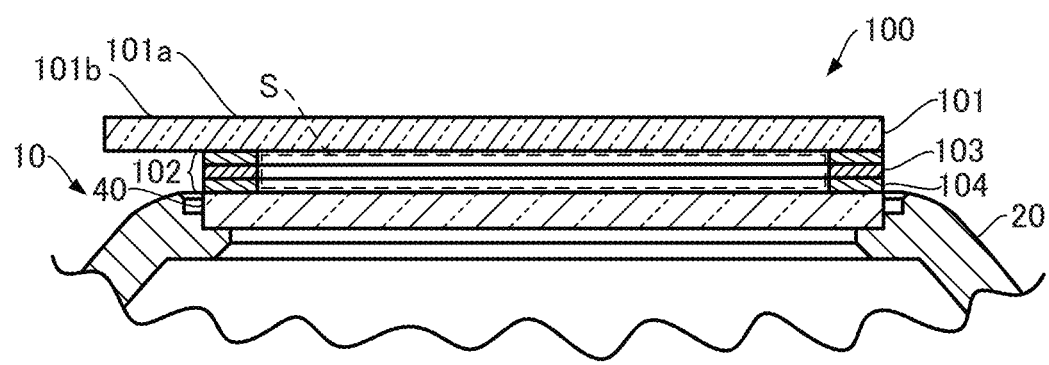
FIG. 7C is a schematic view illustrating how the imaging device cover according to Embodiment 1 of the present disclosure is attached to the imaging device in order of steps.

After attaching the imaging device cover 100 at step S14, the object person peels off the protective member 107 from the cover member 101 (step S15). Between the protective member 107 and the protruding portion 101b of the cover member 101, a step difference h corresponding to the total thickness of the protective member 107 and the third adhesive layer 108 is formed as illustrated in FIG. 7B. The protective member 107 can be easily peeled off from a position where the step difference h is formed. As above, as illustrated in FIG. 7C, the attachment of the imaging device cover 100 is completed, and the cover member 101 can be disposed on the side of the imaging device cover 100 facing the skin disease area.

Subsequently, the object person captures the skin disease area (step S16). When performing dermoscopy imaging of the skin disease area, the object person applies gel to the skin disease area as described above, and presses the object cover 40 attached with the imaging device cover 100 against the skin disease area. Subsequently, after checking that the skin disease area to be imaged is positioned within the capturing assurance region R2 illustrated in FIG. 8A, the object person operates the shutter button 4 (FIG. 1). Thus, the dermoscopy imaging of the skin disease area can be performed. When capturing the skin disease area by normal imaging, the object person separates the imaging device cover 100 and the object cover 40 from the skin disease area, and operates the shutter button 4 (FIG. 1). Thus, the normal imaging of the skin disease area can be performed.

When all skin disease areas of one patient are completely captured in this manner, the object person removes the imaging device cover 100 from the imaging device 1 (step S17). Thus, the imaging by the imaging device 1 ends. Note that the object person can easily remove the imaging device cover 100 by holding the protruding portion 101b illustrated in FIG. 7C with his/her fingers. Thus, the first adhesive layer 104 is peeled off from the object cover 40. In this way, the object cover 40 from which the imaging device cover 100 has been removed is maintained in a sanitary condition because the object cover 40 does not come into contact with a skin disease area during imaging. When capturing a skin disease area of another patient, imaging is performed again according to the flowchart illustrated in FIG. 9.

According to Embodiment 1 described above, dermoscopy imaging can be performed by bringing the object cover 40 close to a skin disease area while covering the object cover 40 with the imaging device cover 100. Thus, the object cover 40 does not come into contact with the skin disease area, and the sanitary condition of the imaging device 1 can be maintained. Thus, there is no need to clean the imaging device 1 each time imaging is terminated, and imaging can be smoothly performed.

Furthermore, since the imaging device cover 100 that comes into contact with a skin disease area can be replaced for each patient, an image of the skin disease area can be taken for examination while considering the sanitation.

Furthermore, the double-sided tape 102 for attaching the imaging device cover 100 is provided only on the cover peripheral portion 101c that is the peripheral portion of the imaging device cover 100. Thus, since no adhesive layer is provided in the capturing assurance region R2, degradation in a captured image due to the adhesive layer can be prevented, and an appropriate image of a diseased area can be captured.

Furthermore, even though a part of the first adhesive layer 104 remains on the object cover 40 when the imaging device cover 100 is removed from the imaging device 1, the remaining first adhesive layer 104 is out of the capturing assurance region R2 and thus does not affect the quality of a captured image. Therefore, even though the imaging device cover 100 is repeatedly replaced, an appropriate image of a diseased area can be continuously captured.

Furthermore, the colored layer 103 colored black can be disposed along the peripheral portion of the imaging device cover 100, and can be checked on the liquid crystal monitor 6 when the imaging device cover 100 is attached. Thus, by checking the state of the colored layer 103 projected on the liquid crystal monitor 6, the imaging device cover 100 can be intuitively guided to a normal position. This makes it possible to easily attach the imaging device cover 100. Furthermore, by adding a color to the colored layer 103, visually recognizing the colored layer 103 through an image on the liquid crystal monitor 6 is facilitated, and positioning of the imaging device cover 100 is facilitated.

Furthermore, by making the colored layer 103 black, the colored layer 103 can be projected in the same color as the support 20 projected darkly on the liquid crystal monitor 6 as illustrated in FIG. 8A. Thus, a captured image that does not give a sense of discomfort can be acquired.

Furthermore, by using the pale green protective member 107, when the imaging device cover 100 is attached, a capturable region projected on the liquid crystal monitor 6 can be made pale green. Thus, the capturable region is easily distinguished from the black colored layer 103, and the imaging device cover 100 can be easily attached while viewing an image displayed on the liquid crystal monitor 6.

Figure 8B:
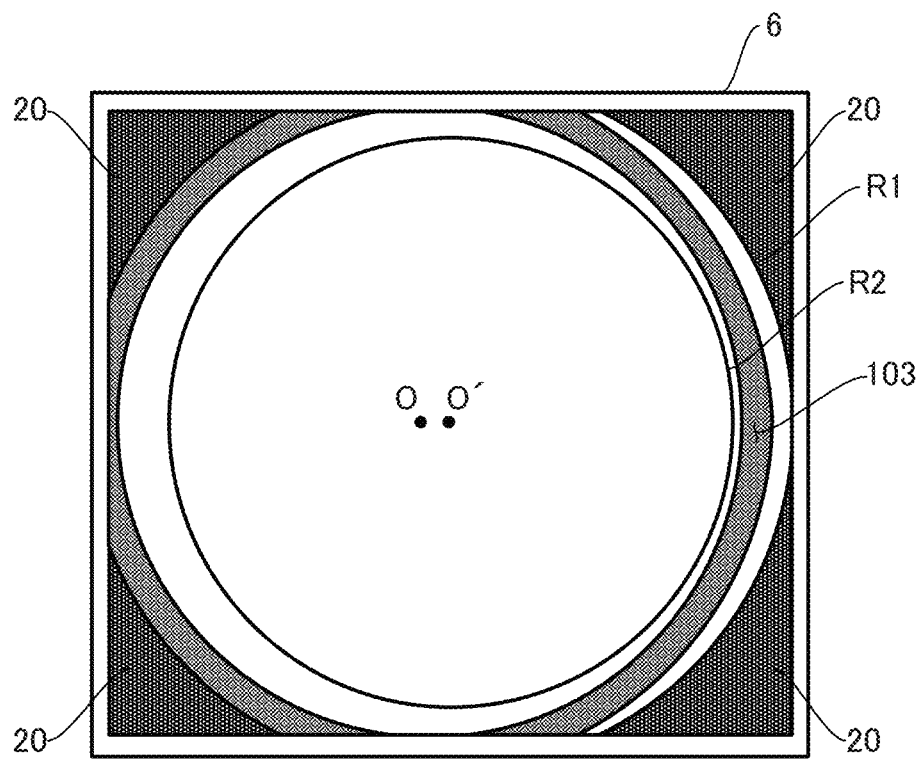
FIG. 8B is an explanatory diagram of an image projected on the liquid crystal monitor when the imaging device cover according to Embodiment 1 of the present disclosure is attached to the imaging device, and is a diagram when the imaging device cover is attached to a position shifted from the normal attachment position.

Furthermore, as illustrated in FIG. 8A, when the imaging device cover 100 is attached to the normal attachment position, an annular gap having a width W3 is formed between an inner edge 103a of the colored layer 103 and an outer edge 110 of the capturing assurance region R2. Thus, even when the attachment position of the imaging device cover 100 is shifted from the normal position, the colored layer 103 can be prevented from blocking the capturing assurance region R2. For example, as illustrated in FIG. 8B, when the attachment position of the imaging device cover 100 is shifted from the normal position to the left in the drawing, the center O of the colored layer 103 formed in an annular shape does not match the center O' of the capturable region R1. Even in such a case, when the amount of shift from the normal position is smaller than the width W3, the colored layer 103 does not cover the capturing assurance region R2 and does not interfere with a captured image.

Furthermore, the first adhesive layer 104 is made of a repeelable acrylic adhesive. Thus, even though the colored layer 103 overlaps the capturing assurance region R2 when the imaging device cover 100 is attached, the imaging device cover 100 can be peeled off, and can be attached again.

Furthermore, since the cover member 101 constituting the imaging device cover 100 is made of a polycarbonate sheet material having a thickness of 188 μm, wrinkles are less likely to occur when the imaging device cover 100 is attached or when an image is taken. Thus, wrinkles formed in the cover member 101 less likely to appear in a captured image, and a skin disease area can be appropriately captured.

Embodiment 2

Figure 10A:
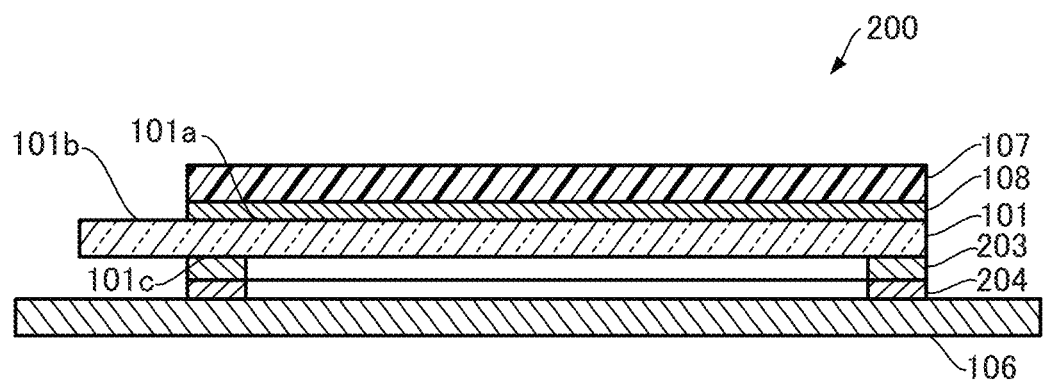
FIG. 10A is a cross-sectional view of an imaging device cover according to Embodiment 2 of the present disclosure.

Next, Embodiment 2 of the present disclosure is described. Since the present embodiment has many configurations in common with Embodiment 1 described above, the same reference numerals are given to the common configurations. As illustrated in FIG. 10A, an imaging device cover 200 has the same configuration as the imaging device cover 100 of Embodiment 1 described above except for a configuration interposed between the cover member 101 and the base sheet 106, specifically, only a configuration including a colored layer 203 and a first adhesive layer 204. That is, the imaging device cover 200 includes the colored layer 203 printed on the cover member 101 and the first adhesive layer 204 seal-printed on the colored layer 203 instead of the double-sided tape 102 as illustrated in FIG. 6.

The colored layer 203 is configured by inkjet printing, with red ink, on the surface of the cover member 101 opposite to the side on which the protective member 107 is provided. The formation range of the colored layer 203 is the same as the hatched region (cover peripheral portion 101c) of the double-sided tape 102 in FIG. 5, and is formed in an annular shape.

The first adhesive layer 204 is made of, for example, a repeelable acrylic adhesive. The first adhesive layer 204 is seal-printed on the colored layer 203 in an annular shape.

Figure 10B:
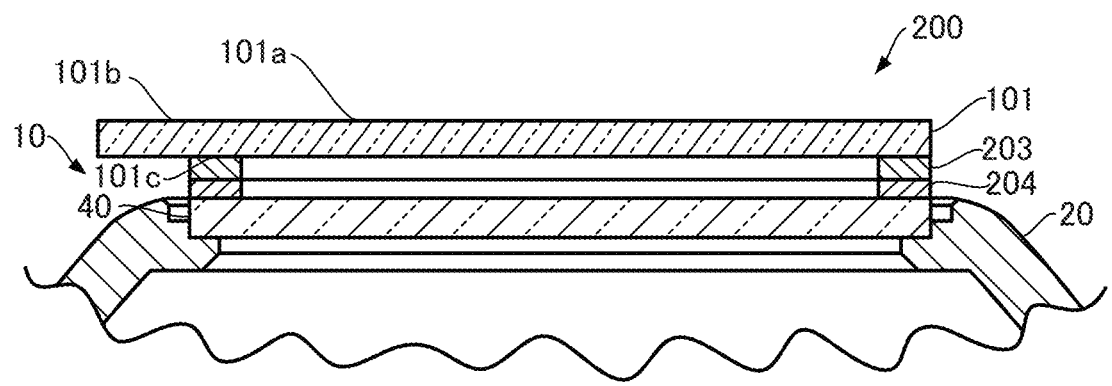
FIG. 10B is a cross-sectional view illustrating a state in which the imaging device cover according to Embodiment 2 of the present disclosure is attached to an imaging device.

Note that a method of attaching the imaging device cover 200 to the imaging device 1 (FIG. 1) is the same as that of the imaging device cover 100 of Embodiment 1. The base sheet 106 is first peeled off, the imaging device cover 200 is positioned, the imaging device cover 200 is then attached to the object cover 40, and the protective member 107 is finally peeled off. Thus, as illustrated in FIG. 10B, the imaging device cover 200 is attached to the object cover 40 via the first adhesive layer 204.

Also in the present embodiment, the same effects as in Embodiment 1 are obtained. Furthermore, since the colored layer 203 is formed of red ink, an image displayed on the liquid crystal monitor 6 (FIGS. 8A and 8B) when the imaging device cover 200 is attached is also displayed in red. Therefore, the colored layer 203 can be easily recognized through the image on the liquid crystal monitor 6 (FIGS. 8A and 8B), and the imaging device cover 200 can be easily positioned.

Embodiment 3

Figure 11A:
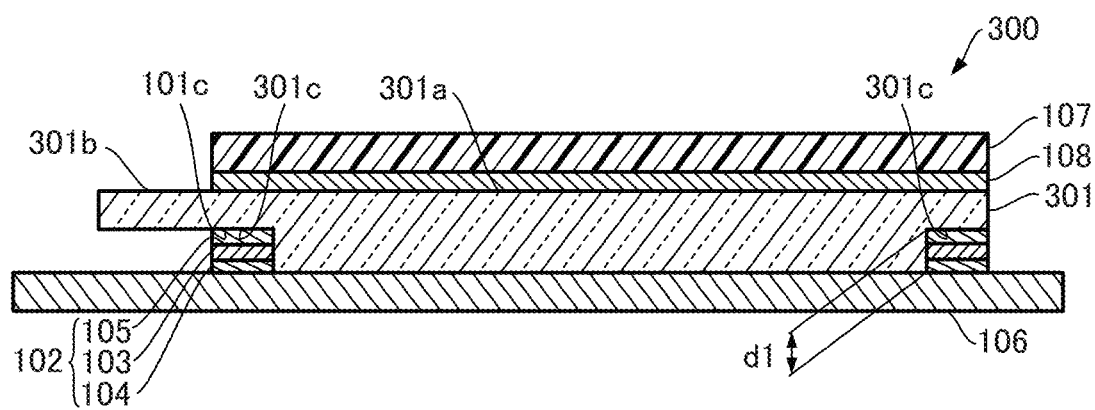
FIG. 11A is a cross-sectional view of an imaging device cover according to Embodiment 3 of the present disclosure.

Next, Embodiment 3 of the present disclosure is described. As illustrated in FIG. 11A, an imaging device cover 300 has the same configuration as the imaging device cover 100 of Embodiment 1 described above except that a cover member 301 is different from the cover member 101 illustrated in FIG. 6.

Figure 11B:
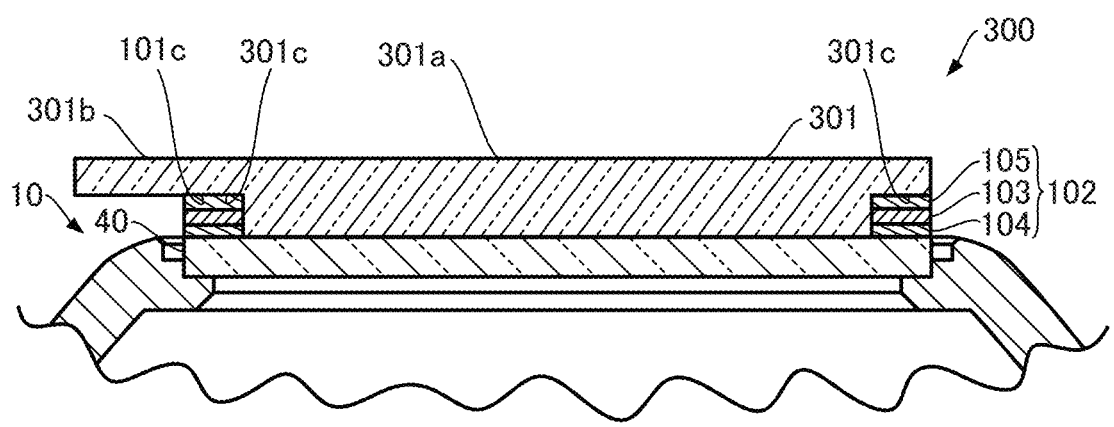
FIG. 11B is a cross-sectional view illustrating a state in which the imaging device cover according to Embodiment 3 of the present disclosure is attached to an imaging device.

The cover member 301 is made of transparent polycarbonate, and includes a thicker sheet material than the cover member 101 illustrated in FIG. 6. As illustrated in FIGS. 11A and 11B, the cover member 301 includes a circular portion 301a having a diameter approximately equal to the diameter of the object cover 40, and a protruding portion 301b protruding outward from an outer edge of the circular portion 301a. Furthermore, an accommodator 301c for accommodating the double-sided tape 102 is formed along the peripheral portion of the circular portion 301a. The accommodator 301c is formed by subjecting a polycarbonate sheet material to numerical control (NC) processing. The accommodator 301c is a recess extending continuously over the entire peripheral portion and is recessed on the opposite side of the object cover 40. The accommodator 301c is formed in an annular shape in correspondence to the cover peripheral portion 101c illustrated in FIG. 5 when viewed in plan, and has a depth d1 approximately equal to the thickness of the double-sided tape 102. Therefore, the double-faced tape 102 accommodated in the accommodator 301c does not protrude from the cover member 301, or even though the double-faced tape 102 protrudes, the amount of protrusion of the double-faced tape 102 with respect to the cover member 301 can be reduced.

Note that a method for attaching the imaging device cover 300 to the imaging device 1 (FIG. 1) is the same as that of the imaging device cover 100 of Embodiment 1. The base sheet 106 is first peeled off, the imaging device cover 300 is positioned, the imaging device cover 300 is then attached to the object cover 40, and the protective member 107 is finally peeled off. Thus, as illustrated in FIG. 11B, the imaging device cover 300 is attached to the object cover 40 via the first adhesive layer 104.

Also in the present embodiment, the same effects as in Embodiment 1 are obtained. Furthermore, by forming the accommodator 301c that is a recess extending continuously over the entire peripheral portion of the cover member 301 and removing or reducing the amount of protrusion of the double-faced tape 102 from the cover member 301, the cover member 301 and the object cover 40 can be brought into contact with each other or a gap between the cover member 301 and the object cover 40 can be reduced as illustrated in FIG. 11B. Thus, the cover member 301 can be held along the object cover 40, and warping of the cover member 301 can be prevented. Thus, an unintended light source can be prevented from appearing in a captured image or the captured image can be prevented from being distorted.

Embodiment 4

Figure 12A:
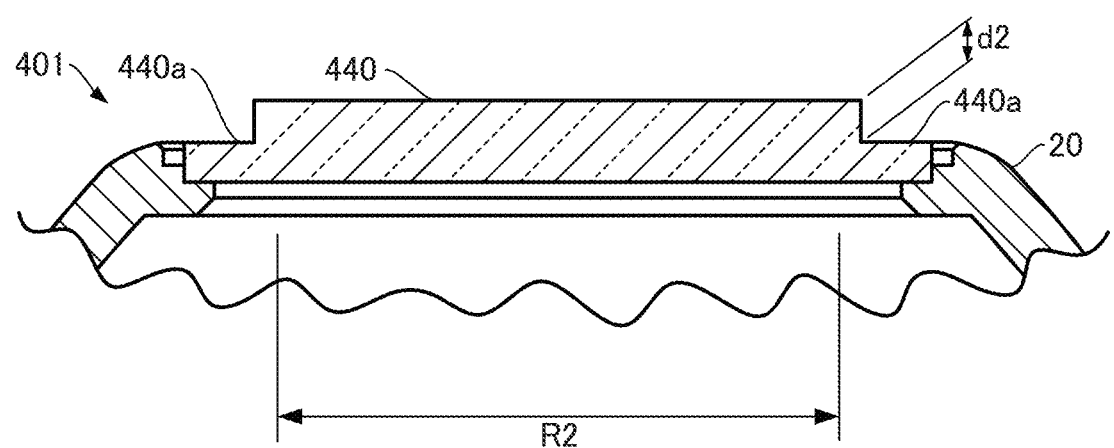
FIG. 12A is a cross-sectional view focusing on an object cover of an imaging device according to Embodiment 4 of the present disclosure.

Next, Embodiment 4 of the present disclosure is described. As illustrated in FIG. 12A, the present embodiment has the same configuration as Embodiment 1 except that only a configuration of an object cover 440 of an imaging device 401 is different from the configuration of the object cover 40 (FIG. 7C) of Embodiment 1.

Figure 12B:
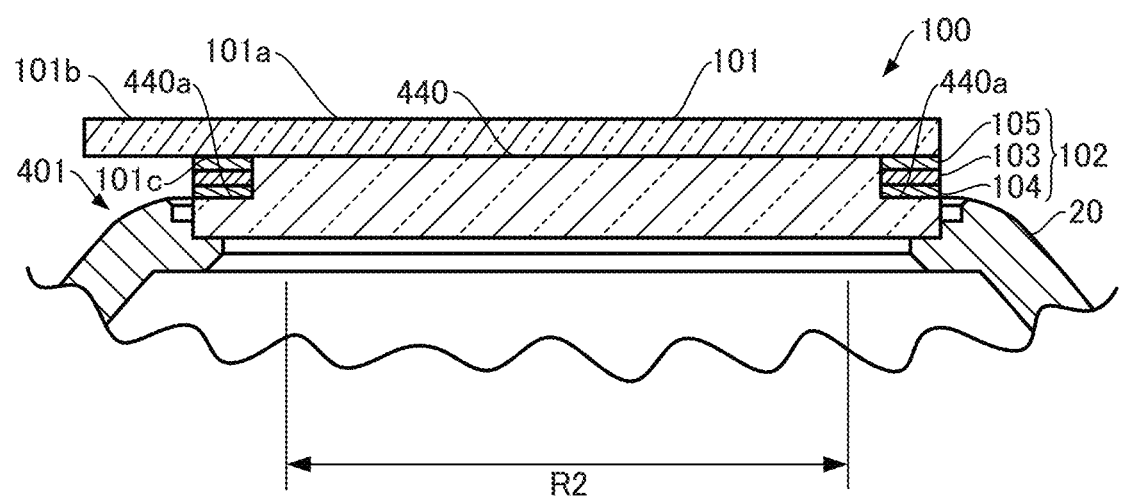
FIG. 12B is a view focusing on the object cover of the imaging device according to Embodiment 4 of the present disclosure, and is a cross-sectional view illustrating a state in which an imaging device cover is attached.

The object cover 440 includes a glass cover formed in a circular shape, similar to the object cover 40 (FIG. 3). As illustrated in FIGS. 12A and 12B, the object cover 440 is formed with an accommodator 440a for accommodating the double-sided tape 102 along the peripheral portion of the object cover 440. The accommodator 440a is a recess extending continuously over the entire peripheral portion of the object cover 440, is formed in an annular shape when viewed in plan, and has a depth d2 approximately equal to the thickness of the double-sided tape 102. Note that the formation region of the accommodator 440a is formed outside the capturing assurance region R2.

Note that a method for attaching the imaging device cover 100 to the imaging device 401 is the same as that of the imaging device cover 100 of Embodiment 1. The base sheet 106 illustrated in FIG. 6 is first peeled off, the imaging device cover 100 is positioned, the imaging device cover 100 is then attached to the object cover 440, and the protective member 107 illustrated in FIG. 6 is finally peeled off. Thus, as illustrated in FIG. 12B, the imaging device cover 100 is attached to the object cover 440 via the first adhesive layer 104.

Also in the present embodiment, the same effects as in Embodiment 1 are obtained. Furthermore, since the object cover 440 is formed with the accommodator 440a for accommodating the double-sided tape 102, the imaging device cover 100 can be attached in a state in which the cover member 101 is brought into contact with a portion of the object cover 440 other than the peripheral portion or in a state in which a gap between the cover member 101 and the portion of the object cover 440 other than the peripheral portion is reduced. Thus, the cover member 101 can be held along the object cover 440, and warping of the cover member 101 can be prevented. Thus, an unintended light source can be prevented from appearing in a captured image or the captured image can be prevented from being distorted.

Furthermore, since the accommodator 440a for accommodating the double-sided tape 102 is formed on the surface of the object cover 440, when the imaging device cover 100 is attached, the accommodator 440a with which the double-sided tape 102 is to coincide can be visually observed, so that the imaging device cover 100 can be easily positioned.

Embodiment 5

Figure 14A:
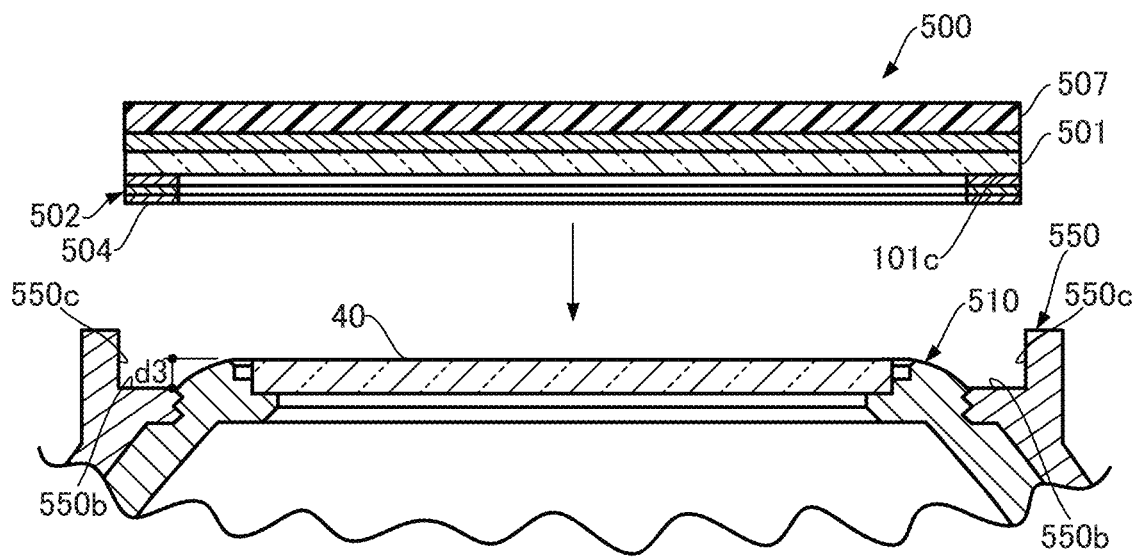
FIG. 14A is a cross-sectional view focusing on an object cover of the imaging device according to Embodiment 5 of the present disclosure.
Figure 14B:
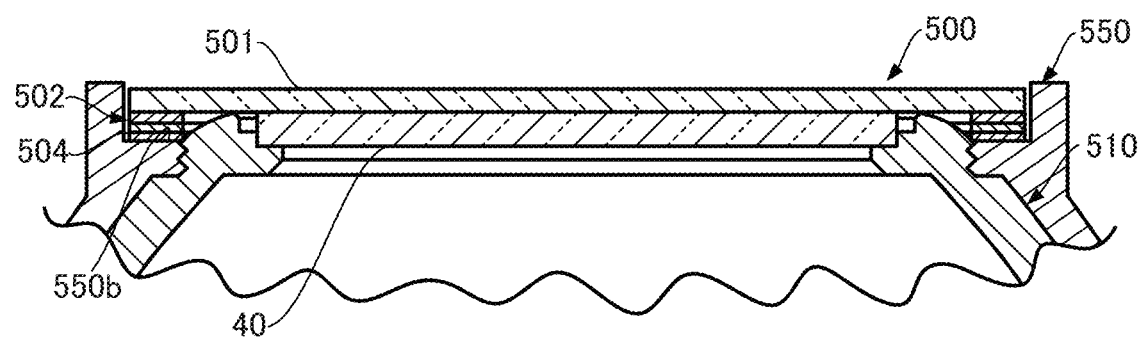
FIG. 14B is a view focusing on the object cover of the imaging device according to Embodiment 5 of the present disclosure, and is a cross-sectional view illustrating a state in which an imaging device cover is attached.

In each of the above-described embodiments, a first adhesive layer for attaching an imaging device cover is attached to an object cover of an imaging device; however, in Embodiment 5, as illustrated in FIG. 14B, a first adhesive layer is attached to an attachment 550 attached to a cover structure 510.

Figure 13:
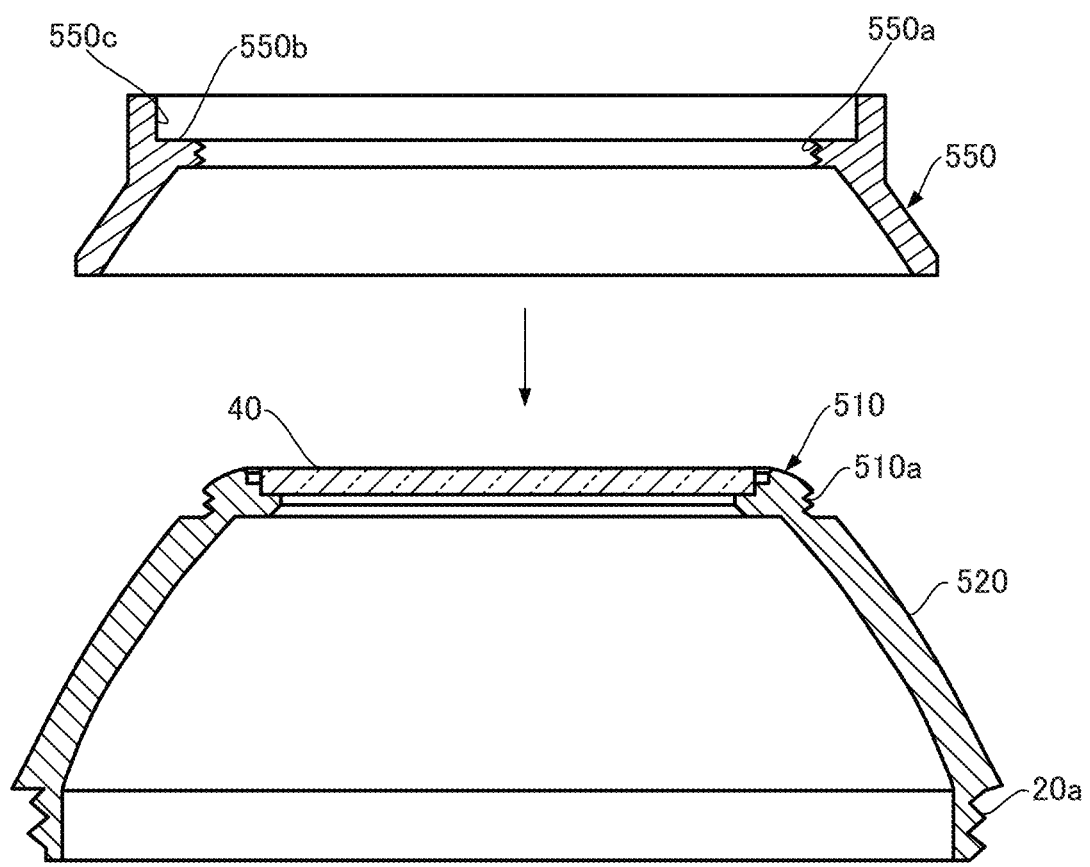
FIG. 13 is a cross-sectional view focusing on a cover structure and an attachment of an imaging device according to Embodiment 5 of the present disclosure.

As illustrated in FIG. 13, a male thread 510a for attaching the attachment 550 is formed on an outer peripheral surface of the cover structure 510 and around the object cover 40. A female thread 550a is formed on an inner peripheral surface of the attachment 550. The attachment 550 is attached to the cover structure 510 by screwing the male thread 510a into the female thread 550a.

The attachment 550 is a tubular member having an enlarged diameter toward the camera body 3 side, and covers a part of the outer peripheral surface of the cover structure 510. The attachment 550 is provided at a front end thereof with an attachment surface portion 550b to which the first adhesive layer 504 of an imaging device cover 500 illustrated in FIG. 14A is attached, and an upright portion 550c installed vertically from the attachment surface portion 550b.

The attachment surface portion 550b is formed in an annular shape in accordance with the shape of the first adhesive layer 504 formed in an annular shape. As illustrated in FIG. 14B, the attachment surface portion 550b is formed at a position recessed by a depth d3 from a surface of the object cover 40 on a skin disease area side. That is, the attachment surface portion 550b is formed at a position recessed toward the imaging lens system 7 (FIG. 2) from the object cover 40. The depth d3 is approximately equal to the thickness of a double-sided tape 502 of the imaging device cover 500.

The upright portion 550c is a portion installed vertically from an outer edge of the attachment surface portion 550b toward a skin disease area side and formed in a cylindrical shape, and accommodates the imaging device cover 500 therein. Since a region surrounded by the upright portion 550c roughly matches an outer shape of the imaging device cover 500, the object person can recognize the attachment position of the imaging device cover 500 by checking the upright portion 550c. The upright portion 550c prevents the position displacement of the imaging device cover 500 in contact with the outer edge of the imaging device cover 500.

To attach the imaging device cover 500 to the cover structure 510 to which the attachment 550 is attached, as illustrated in FIG. 14B, the imaging device cover 500, from which a base sheet (not illustrated) has been peeled off, is first brought closer to the cover structure 510 for positioning. The imaging device cover 500 can be positioned by allowing the imaging device cover 500 to match the region surrounded by the upright portion 550c. Then, the first adhesive layer 504 is attached to the attachment surface portion 550b of the attachment 550. Finally, the protective member 107 illustrated in FIG. 14A is peeled off. Thus, as illustrated in FIG. 14B, the imaging device cover 500 can be attached to the cover structure 510, to which the attachment 550 is attached, via the first adhesive layer 504.

In the present embodiment, the configuration in which the cover structure 510 and the attachment 550 are separate bodies has been described; however, an integral configuration in which the cover structure 510 has a configuration corresponding to the attachment 550 may be adopted. Thus, the attachment/detachment work of the attachment 550 can be omitted. Furthermore, the upright portion 550c rising from the attachment surface portion 550b may be omitted. Even in such a case, since the attachment surface portion 550b having an annular shape is formed in a recessed position, the attachment surface portion 550b is easy to be visually recognized. Therefore, by allowing the first adhesive layer 504 to match the attachment surface portion 550b, the imaging device cover 500 can be easily positioned at the normal position.

Also in the present embodiment, the same effects as in Embodiment 1 are obtained. Furthermore, the attachment surface portion 550b formed on the attachment 550 is formed at a position recessed by the depth d3 from the surface of the object cover 40 on a skin disease area side. Thus, as illustrated in FIG. 14B, the double-sided tape 502 can be provided in the recessed region, and the imaging device cover 500 can be attached in a state in which the cover member 501 is brought into contact with the object cover 40 or in a state in which a gap between the cover member 501 and the object cover 40 is reduced. Thus, warping of the cover member 501 can be prevented, and an unintended light source can be prevented from appearing in a captured image or the captured image can be prevented from being distorted.

When the imaging device cover 500 is positioned, the region surrounded by the upright portion 550c with which the imaging device cover 500 is to coincide can be visually observed, and the positioning can be easily performed. Furthermore, since the imaging device cover 500 that has been positioned and placed can be surrounded by the upright portion 550c, the positioned imaging device cover 500 is not displaced. Therefore, the attachment work of the imaging device cover 500 can be performed easily and reliably.

Embodiment 6

Figure 15:
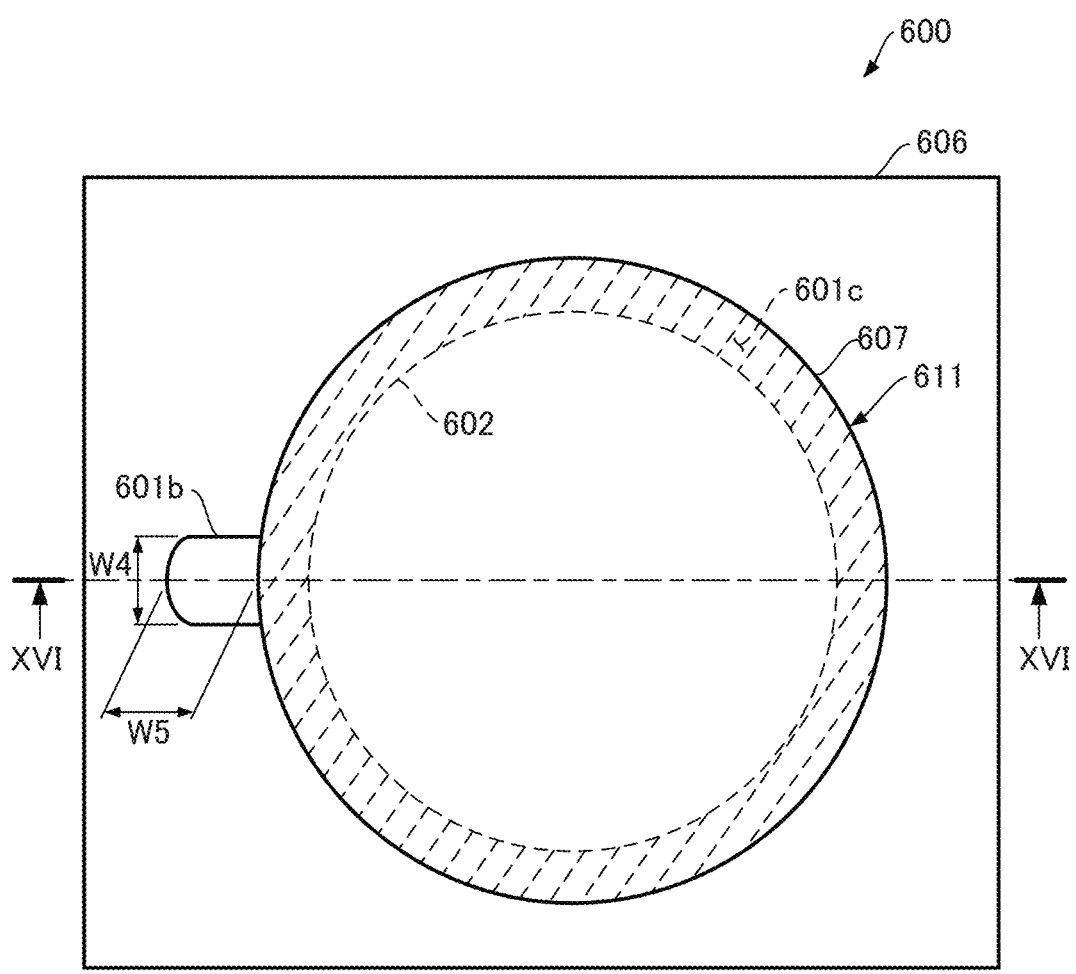
FIG. 15 is a plan view of an imaging device cover according to Embodiment 6 of the present disclosure.
Figure 16:
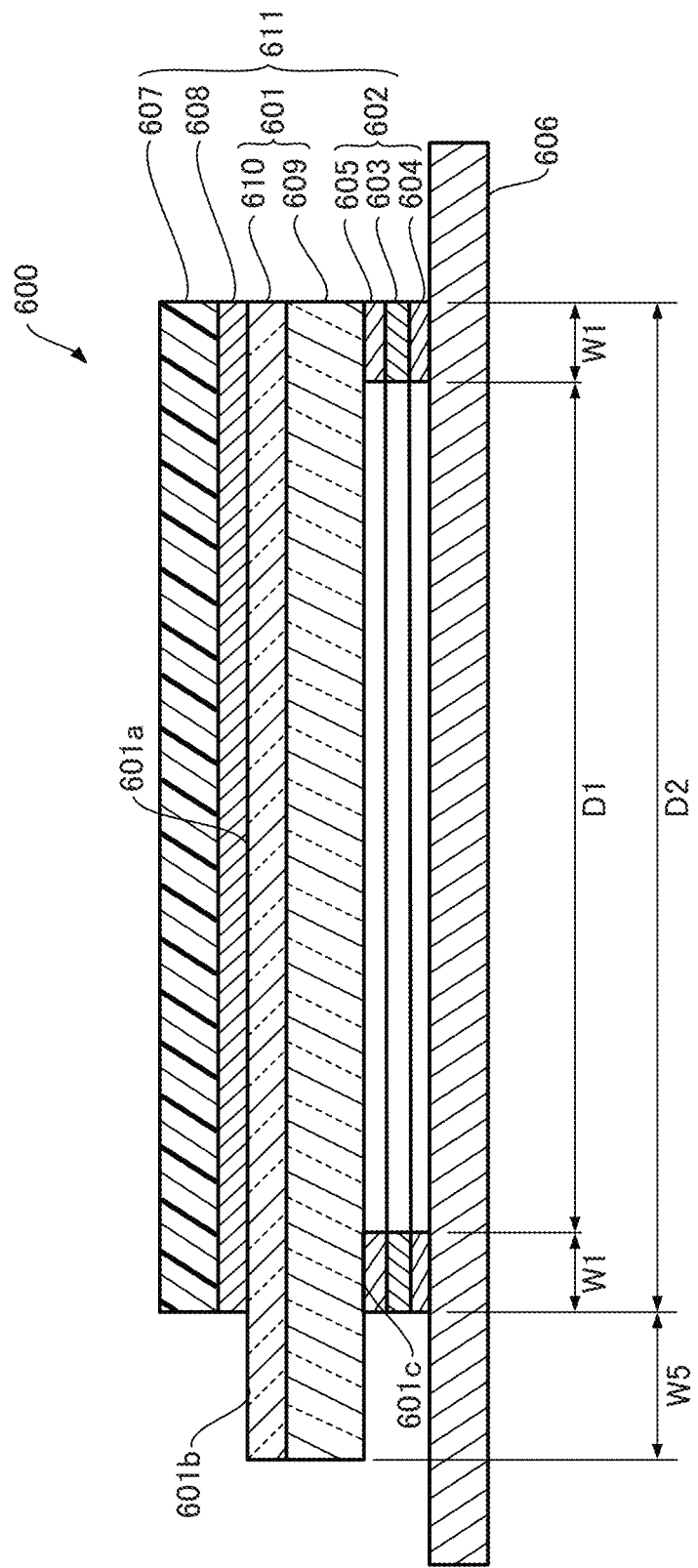
FIG. 16 is a cross-sectional view of the imaging device cover viewed from the cross-sectional line XVI-XVI in FIG. 15.

An imaging device cover 600 of Embodiment 6 has many configurations in common with the imaging device cover 100 of Embodiment 1. Therefore, points different from the configuration of Embodiment 1 are mainly described below. In Embodiment 1 described above, a cover member is made of polycarbonate; however, as illustrated in FIG. 16, the imaging device cover 600 in Embodiment 6 includes a cover member 601 made of two different materials. That is, the cover member 601 includes a stacked body in which a first layer 609 made of polycarbonate and a second layer 610 made of acrylic resin are integrated. The first layer 609 is disposed on a double-sided tape 602 side and has a thickness of, for example, 265 μm. The second layer 610 is disposed on a protective member 607 side and has a thickness of, for example, 35 μm. Thus, the total thickness of the cover member 601 is, for example, 300 μm. The first layer 609 and the second layer 610 are formed to have the same shape as each other, and each include a circular portion 601a having a diameter D2 approximately equal to the diameter of the object cover 40 (FIG. 18), and a protruding portion 601b protruding outward from an outer edge of the circular portion 601a. This point is the same as Embodiment 1 described above. The diameter D2 of the circular portion 601a is, for example, 32.4 mm. An amount W5 of protrusion of the protruding portion 601b outward is, for example, 6.8 mm. As illustrated in FIG. 15, a width W4 of the protruding portion 601b in the direction orthogonal to the protruding direction is, for example, 7 mm.

The double-sided tape 602 includes a second adhesive layer 605, a colored layer 603, and a first adhesive layer 604, which are each formed in an annular shape, like the double-sided tape 102 (FIG. 6) of Embodiment 1. The double-sided tape 602 is attached to the first layer 609 of the cover member 601 via the second adhesive layer 605. The colored layer 603 has a thickness of, for example, 16 μm, and the first adhesive layer 604 and the second adhesive layer 605 each have a thickness of, for example, 17 μm. That is, the total thickness of the double-sided tape 602 is, for example, 50 μm. A width W1 of the double-sided tape 602 is set to, for example, 4.55 mm. An inner diameter D1 of the double-sided tape 602 is, for example, 23.3 mm. The value of the inner diameter D1 is a value smaller than the diameter of the capturable region R1 and larger than the diameter of the capturing assurance region R2 illustrated in FIG. 3. The double-sided tape 602 is peelably attached to a base sheet 606 via the first adhesive layer 604.

Note that the configuration of the base sheet 606 is the same as the configuration of the base sheet 106 of Embodiment 1 illustrated in FIG. 6.

The protective member 607 is made of a light-transmissive material, such as a polyethylene terephthalate sheet material having a thickness of 50 μm. The protective member 607 is formed in a circular shape and has the same diameter as the diameter D2 of the circular portion 601a of the cover member 601. The protective member 607 is colored blue, for example, and covers and protects the cover member 601 until the cover member 601 is removed at the time of imaging.

A third adhesive layer 608 has the same configuration and function as those of the protective member 107 illustrated in FIG. 6, and attaches the protective member 607 to the cover member 601 in a peelable manner. The third adhesive layer 608 has a thickness of, for example, 30 μm.

For imaging with such an imaging device using the imaging device cover 600, the same method as that for imaging with the imaging device 1 described with reference to FIG. 9 can be used.

Next, the reason why the thickness of the cover member 601 is set to 300 μm is described. For example, when the imaging device cover 100 of Embodiment 1 illustrated in FIG. 6 is attached to the imaging device 1 in the order illustrated in FIGS. 7A to 7C, the cover member 101 is installed on the object cover 40 while being supported by the double-sided tape 102 having an annular shape as illustrated in FIG. 7C. In such a case, a gap S surrounded by the double-sided tape 102 is formed between the cover member 101 and the object cover 40. That is, the gap S corresponding to the thickness of the double-sided tape 102 is formed between the cover member 101 and the object cover 40. The same also applies to the imaging device cover 600 in Embodiment 6 in which the imaging device cover 600 is attached to the object cover 40 by using the double-sided tape 602 having an annular shape. That is, when the imaging device cover 600 illustrated in FIG. 16 is attached to the imaging device 1, the gap S corresponding to the thickness 50 μm of the double-sided tape 602 is formed over a circular region having the inner diameter D1 of the double-sided tape 602, that is, a diameter of 23.3 mm.

When dermoscopy imaging of a skin disease area is performed, the cover member 601 pressed against the skin disease area bends toward the gap S. In such a case, when the maximum bending of the cover member 601 reaches the thickness (for example, 50 μm) of double-sided tape 602, the cover member 601 comes into contact with the object cover 40 as in the state illustrated in FIG. 18B. In the region where the cover member 601 comes into contact with the object cover 40 in this way, an air layer between the cover member 601 and the object cover 40 becomes extremely thin and approaches the wavelength of transmitted light. As a result, light reflected by the cover member 601 and light reflected by the object cover 40 may interfere with each other to generate interference fringes. In this regard, in order to prevent the cover member 601 from coming into contact with the object cover 40 during dermoscopy imaging, bending toward the gap S needs to be suppressed by ensuring a desired bending rigidity for the cover member 601. In this regard, a member to be used for the cover member 601 is determined as described below.

Figure 17:
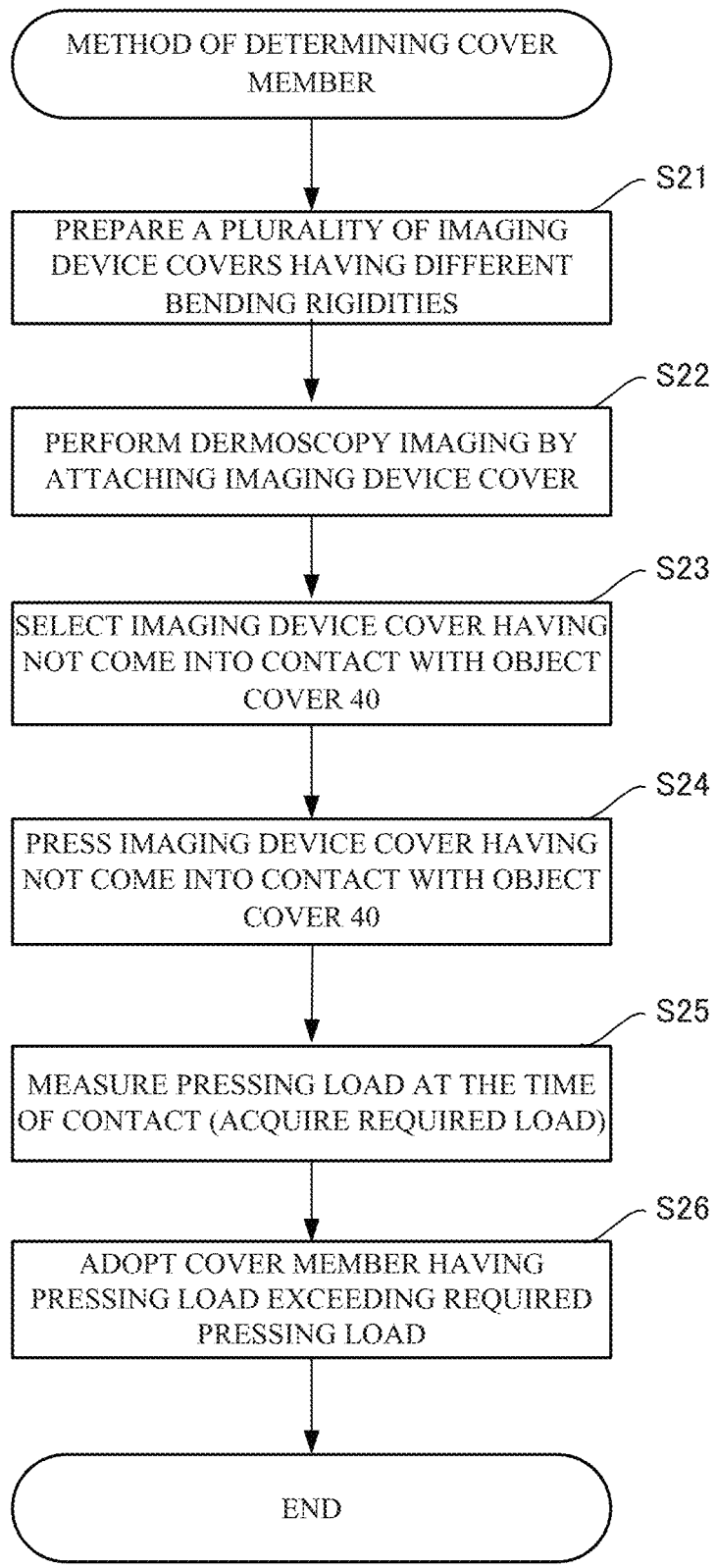
FIG. 17 is a flowchart illustrating a method of determining a cover member of the imaging device cover according to Embodiment 6 of the present disclosure.

First, as illustrated in FIG. 17, a plurality of imaging device covers having different bending rigidities is prepared (step S21). Specifically, a plurality of imaging device covers having the same conditions except for the bending rigidity of a cover member is prepared. Note that the bending rigidity can be varied by varying the thickness or material of the cover member. Note that other conditions set to the same conditions are the material and various dimensions of the double-sided tape 602 and the planar dimensions of the cover member.

Subsequently, the plurality of prepared imaging device covers is attached to the imaging device 1 (FIG. 1), dermoscopy imaging of a skin disease area is performed (step S22), and whether the cover member comes into contact with the object cover 40 is checked. Note that a method of the dermoscopy imaging using the imaging device 1 (FIG. 1) is as described with reference to FIG. 9. For the dermoscopy imaging, when the plurality of prepared imaging device covers is attached to the imaging device 1 in ascending order of bending rigidity, a cover member having a minimum bending rigidity, which does not come into contact with the object cover 40, is easily found.

Subsequently, at step S22, an imaging device cover having not come into contact with the object cover 40 during the dermoscopy imaging is selected (step S23). Whether the cover member has come into contact with the object cover 40 can be determined on the basis of a captured image projected on the liquid crystal monitor 6 illustrated in FIG. 2.

Figure 18A:
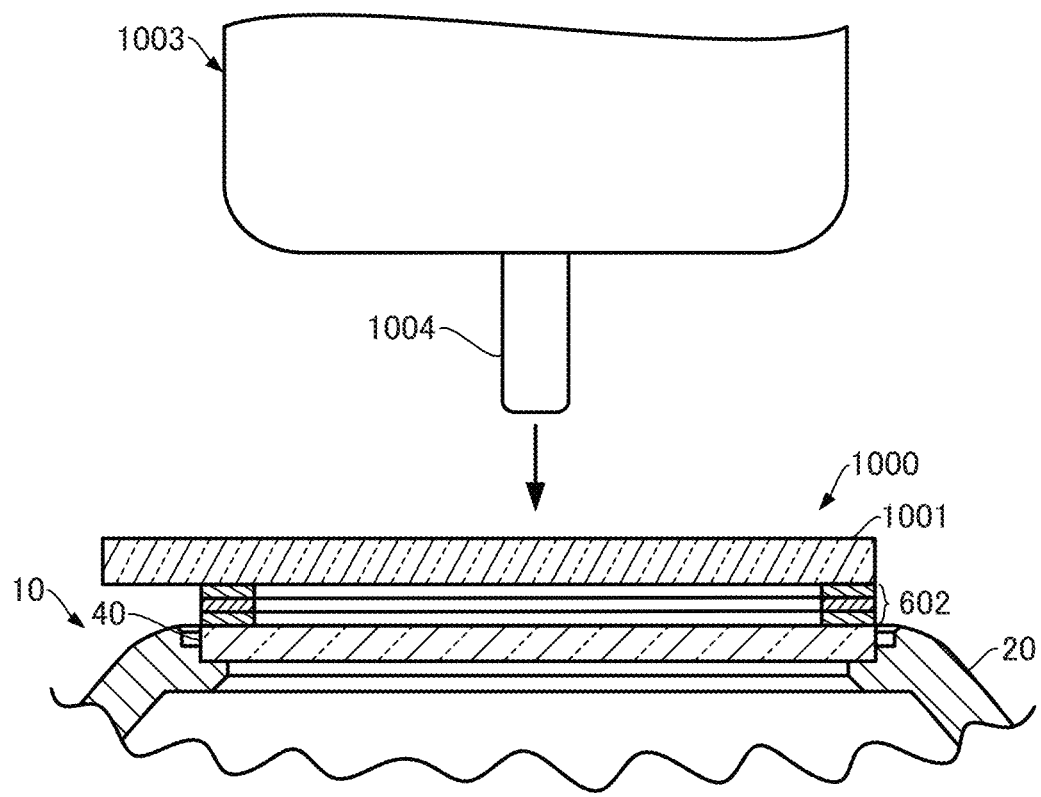
FIG. 18A is an explanatory view illustrating, in order of steps, how the cover member is pressed by a push-pull gage when the cover member is determined.

Subsequently, the imaging device cover selected at step S23 is pressed by a measuring device (step S24). In relation to the pressing of the imaging device, as illustrated in FIG. 18A, in a state in which the center of a cover member 1001 of an imaging device cover 1000 selected at step S23 is attached to the object cover 40, the center of the cover member 1001 is pressed by a pressing portion 1004 of a push-pull gauge 1003. The reason for pressing the center of the cover member 1001 is because the center of the cover member 1001 supported by the double-sided tape 602 having an annular shape is most likely to be bent.

Figure 18B:
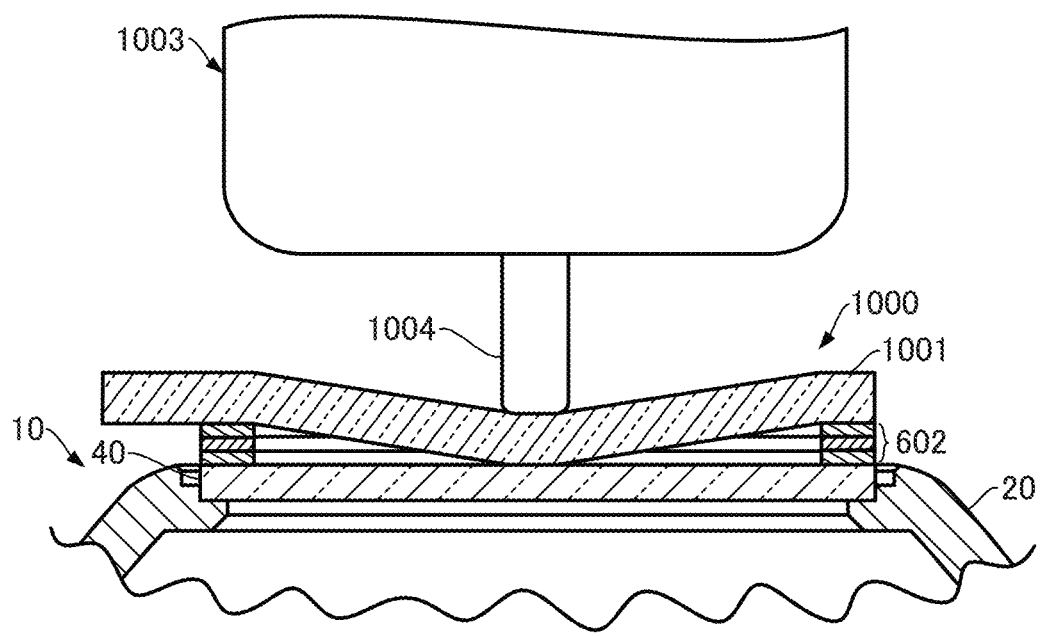
FIG. 18B is an explanatory view illustrating, in order of steps, how the cover member is pressed by the push-pull gage when the cover member is determined.

Subsequently, the pressing portion 1004 is gradually pushed into the cover member 1001, and as illustrated in FIG. 18B, the pressing load at the time when the cover member 1001 is bent and comes into contact with the object cover 40 is measured (step 25). When the pressed cover member 1001 comes into contact with the object cover 40, the object cover 40 as well as the cover member 1001 resists the pressing of the push-pull gauge 1003. Thus, the pressing load indicated by the push-pull gauge 1003 increases with a greater inclination than before the pressed cover member 1001 comes into contact with the object cover 40. Whether the cover member 1001 has come into contact with the object cover 40 can be determined on the basis of the rate of change per unit time of the pressing load indicated by the push-pull gauge 1003. The pressing load at the time when the cover member 1001 has come into contact with the object cover 40 is read from a value immediately before the value indicated by the push-pull gauge 1003 increases. Among the pressing loads measured in this way, the lowest pressing load is measured from an imaging device cover having the lowest bending rigidity among the imaging device covers that do not come into contact with the object cover 40 during the dermoscopy imaging. Therefore, the lowest pressing load is set as a required pressing load (reference pressing load) required when a cover member comes into contact with the object cover 40. That is, when a pressing load equal to or greater than the required pressing load is required for the cover member pressed by the measuring device to come into contact with the object cover 40, the measured cover member can be determined to have a desired bending rigidity.

Next, when a cover member for which whether the cover member comes into contact with the object cover 40 during the dermoscopy imaging is unclear is to be adopted as an imaging device cover, the pressing load when the cover member comes into contact with the object cover 40 is measured as described with reference to FIGS. 18A and 18B, and the cover member having the measured pressing load exceeding the required pressing load is adopted as a cover member for an imaging device cover (step S26). Thus, when the required pressing load of the cover member is determined in advance, whether the cover member has the desired bending rigidity can be determined only by measuring the pressing load when the cover member comes into contact with the object cover 40.

In the imaging device cover in the present embodiment, step S21 to step 25 illustrated in FIG. 17 are performed, and for example, 2.0N is measured as the required pressing load required when the cover member comes into contact with the object cover 40. However, in the cover member 601 with a total thickness of 300 μm in which the first layer 609 made of polycarbonate and the second layer 610 made of acrylic resin are integrated as illustrated in FIG. 16, the pressing load when the cover member 601 comes into contact with the object cover 40 is 2.2N and exceeds the required pressing load of 2.0N. Therefore, the cover member 601 can be determined to have the desired bending rigidity that prevents contact with the object cover 40. For confirmation, the imaging device cover 600 is attached to the imaging device 1 and dermoscopy imaging is performed, but the cover member 601 does not come into contact with the object cover 40. On the other hand, in a cover member (thinner than the cover member 601) with a total thickness of 200 μm in which a layer made of polycarbonate and a layer made of acrylic resin are integrated in the same manner, the pressing load when the cover member has come into contact with the object cover 40 is 1.4 N and becomes less than the required pressing load of 2.0N. Therefore, it can be determined that a cover member having a thickness of 200 μm does not have the desired bending rigidity and may come into contact with the object cover 40 during dermoscopy imaging and interfere with a captured image. For confirmation, when an imaging device cover using the cover member with a thickness of 200 μm is attached to the imaging device 1 and dermoscopy imaging is performed, the cover member comes into contact with the object cover 40.

At step S21 of FIG. 17, an imaging device cover to be actually used is prepared, and at step S23, when an imaging device cover that does not actually come into contact with the object cover 40 during dermoscopy imaging can be selected, the imaging device cover can be used for the dermoscopy imaging, and steps after step S24 are unnecessary.

At step S22 illustrated in FIG. 17, whether the cover member comes into contact with the object cover 40 is determined on the basis of the captured image; however, the determination may be made on the basis of an image (what is called a live view image) displayed on the liquid crystal monitor 6 (FIG. 2) serving as a finder to determine the composition.

At step S25 illustrated in FIG. 17, whether the cover member 1001 has come into contact with the object cover 40 is determined on the basis of a change in the pressing load indicated by the push-pull gauge 1003; however, whether the cover member 1001 has actually come into contact with the object cover 40 may be determined by viewing the pressed cover member 1001, or the determination may be made on the basis of both the change in the pressing load and the appearance of the pressed cover member 1001.

Furthermore, when the conditions other than the bending rigidity of a cover member, such as the material and various dimensions of a double-sided tape and the planar dimensions of the cover member, are varied, the required pressing load measured at step S25 of FIG. 17 also has a different value. Particularly, a clearance between a cover member and an object cover can be easily changed by changing the thickness of a double-sided tape. Consequently, when these conditions are changed, the steps illustrated in FIG. 17 need to be performed again to determine a cover member.

According to the above embodiment, the desired bending rigidity that prevents contact with the object cover 40 during dermoscopy imaging is ensured for the cover member 601 (for example, ensured by setting a thickness of 300 μm). Therefore, light interference fringes caused by a contact of the cover member 601 with the object cover 40 can be prevented, which makes it possible to suppress degradation in the quality of a captured image.

Furthermore, the bending of the cover member 601 toward the gap S can be suppressed, which makes it possible to suppress the occurrence of visually recognizable distortion in a captured image.

When the bending of the cover member toward the gap S increases, internal pressure in the gap sealed by the double-sided tape increases, and the air in the gap may eventually be pushed out to the outside. In this way, once the air in the gap is pushed out to the outside, even though the cover member is released from being pressed against a skin disease area, the cover member may remain in a bent state without returning to the original state, that is, may remain in an adsorbed state. On the other hand, in the above embodiment, the bending of the cover member 601 can be suppressed, so that an adsorbed state is less likely to occur. Thus, phenomena such as interference fringes always appearing in a captured image and visually recognizable distortion always occurring in a captured image due to the occurrence of an adsorbed state can be suppressed.

At step S25 of FIG. 17, by determining the required pressing load of the cover member 601 in advance, whether cover members made of different materials have an appropriate bending rigidity can be determined only by pressing the cover members using a push-pull gauge. Thus, degradation in the quality of a captured image can be suppressed only by performing simple check work.

The cover member 601 includes a stacked body in which the first layer 609 made of polycarbonate and disposed on the double-sided tape 602 side and the second layer 610 made of acrylic resin and disposed on the protective member 607 side are integrated. Thus, the cover member 601 may have both contradictory physical properties such as enhanced impact resistance with polycarbonate and enhanced surface hardness and bending rigidity with acrylic resin. Furthermore, since the second layer 610 made of acrylic resin and having a high surface hardness is disposed on a side of an object to be imaged, the surface of the cover member 601 is less likely to be damaged at the time of imaging, and degradation in the quality of a captured image can be suppressed.

Embodiment 7

Next, Embodiment 7 of the present disclosure is described. In the above embodiment, for example, as illustrated in FIG. 15, the imaging device cover 600 in which one adhesive cover 611 is provided on one base sheet 606 has been described. Note that the adhesive cover 611 is a portion of the imaging device cover 600 excluding the base sheet 606 as illustrated in FIG. 16. On the other hand, in an imaging device cover 700 according to the present embodiment, one base sheet 706 is provided with six adhesive covers 611 as illustrated in FIG. 19.

Figure 19:
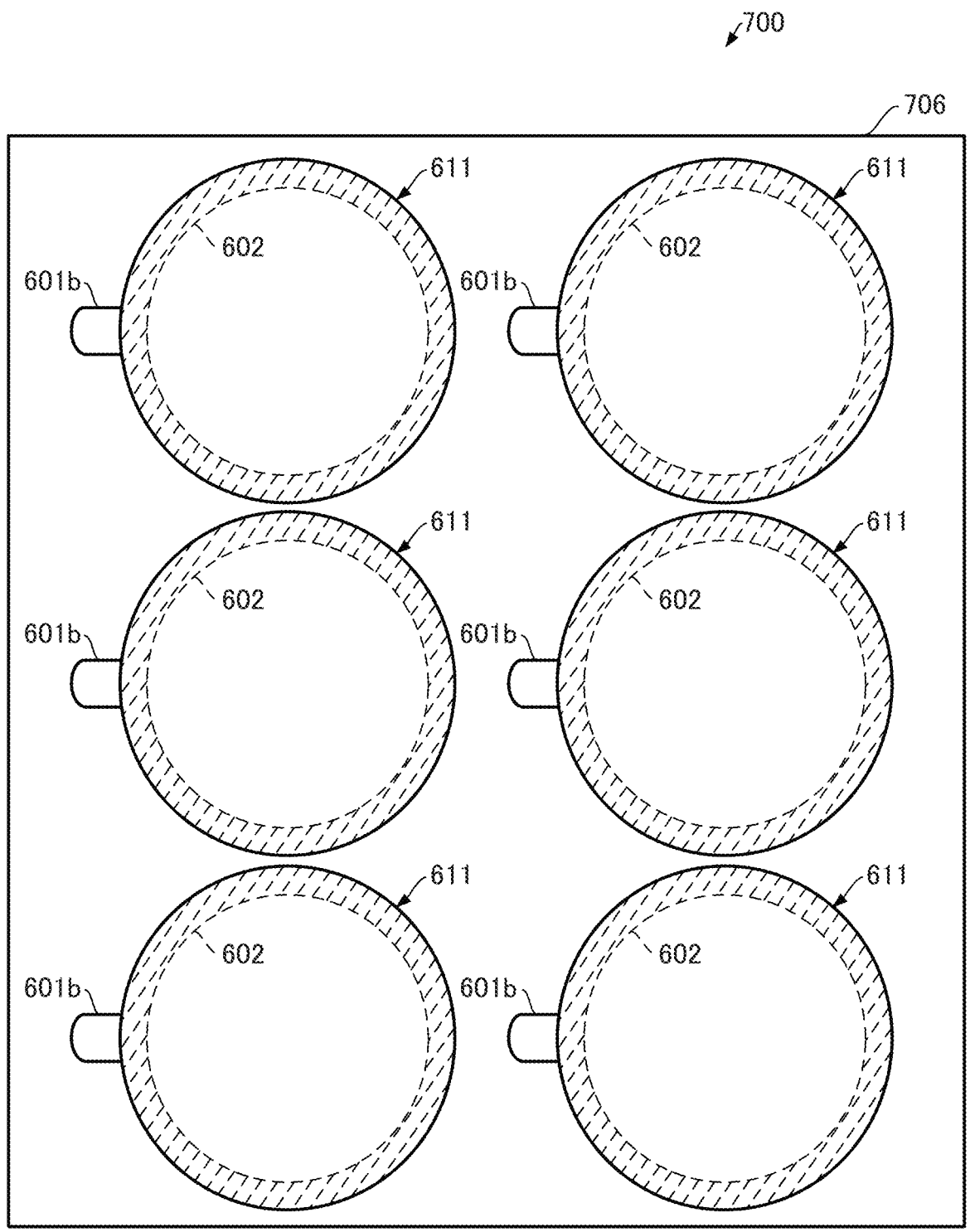
FIG. 19 is a plan view of an imaging device cover according to Embodiment 7 of the present disclosure.

The base sheet 706 illustrated in FIG. 19 is rectangular, and has a length of, for example, 105 mm in the vertical direction and 100 mm in the horizontal direction in the drawing. On the base sheet 706, a total of six adhesive covers 611 are disposed in a matrix form in three rows in the vertical direction and two rows in the horizontal direction. Note that protruding portions 601*b* respectively formed on the six adhesive covers 611 are all directed leftward in the drawing and directed in the same direction.

According to the above embodiment, since the plurality of adhesive covers 611 is provided on one base sheet 706, the trouble of exchanging the base sheet 706 each time an imaging device cover is replaced can be reduced, and a skin disease area of another patient can be smoothly captured. Furthermore, since the protruding portions 601*b* formed on the adhesive covers 611 are all directed in the same direction, an object person (user) can easily recognize the protruding portion 601*b*, and can easily hold the protruding portion 601*b* when peeling off the adhesive cover 611 from the base sheet 706. Thus, a skin disease area can be smoothly captured.

Embodiment 8

Next, Embodiment 8 of the present disclosure is described with reference to FIGS. 20 and 21. The present embodiment is different from the above embodiments in that an optical liquid material applied is interposed between an imaging device cover and an object cover and imaging is performed, that is, the flowchart illustrated in FIG. 20 includes step S10 and step S18 in addition to step S11 to step S17 compared to the flowchart illustrated in FIG. 9. In the present embodiment, the following description is given for a case in which the imaging device cover 600 (FIG. 16) of Embodiment 6 is attached to the imaging device 401 (FIG. 12) of Embodiment 4, in which a cover member and an object cover have come into contact with each other or a gap between the cover member and the object cover can be reduced.

Figure 20:
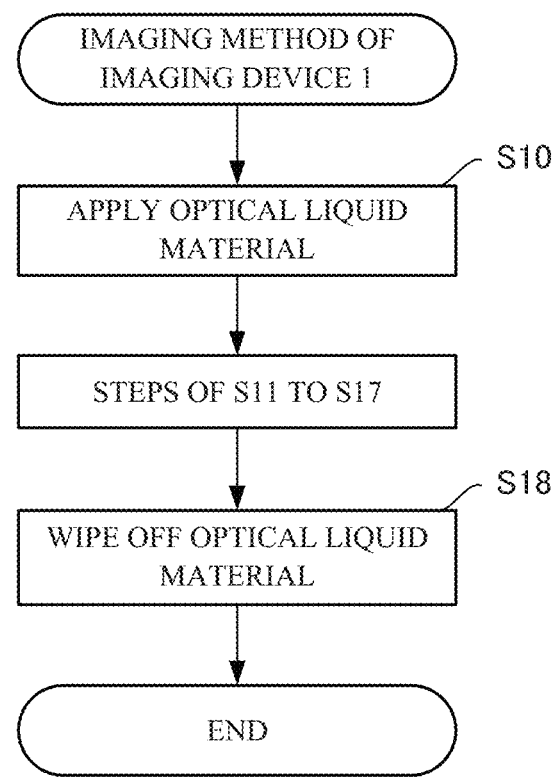
FIG. 20 is a flowchart illustrating an imaging method of an imaging device according to Embodiment 8 of the present disclosure.
Figure 21A:
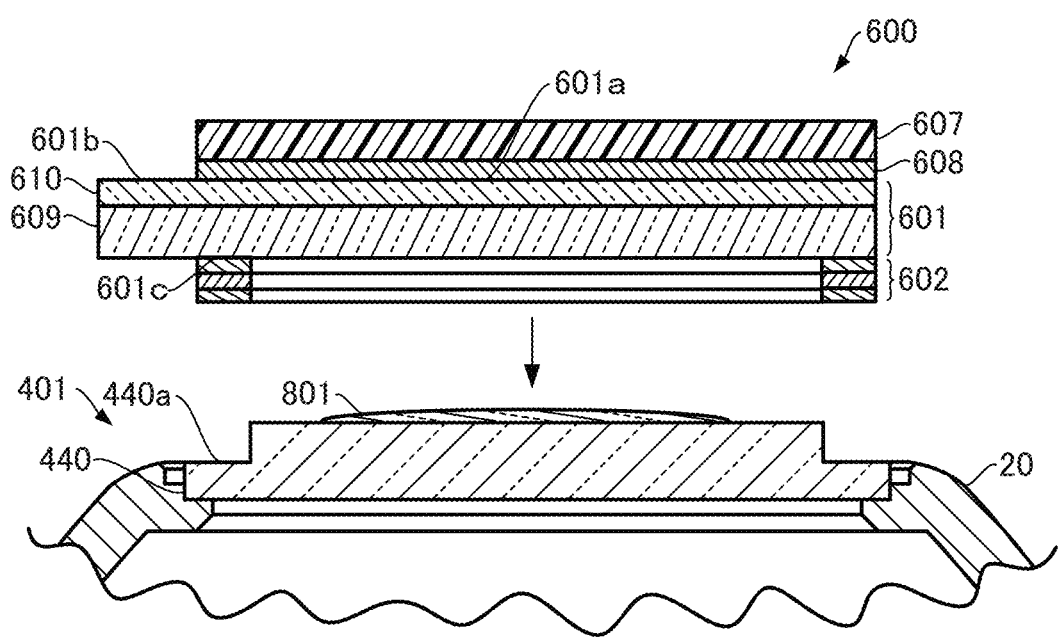
FIG. 21A is a schematic view illustrating how an imaging device cover according to Embodiment 8 of the present disclosure is attached to the imaging device in order of steps.

In the imaging method of the imaging device 1 using the imaging device cover 600, an optical liquid material 801 is first applied to the object cover 440 (step S10) as illustrated in FIG. 20. As illustrated in FIG. 21A, the optical liquid material 801 is applied to a region around the center of the object cover 440, and the region corresponds to a region where the double-sided tape 602 of the imaging device cover 600 is not formed (region of the object cover 440 other than the peripheral portion). The optical liquid material 801 to be applied is preferably selected from materials having a refractive index close to the refractive index (for example, 1.584) of the first layer 609 made of polycarbonate, and is made of, for example, epoxy.

Figure 21B:
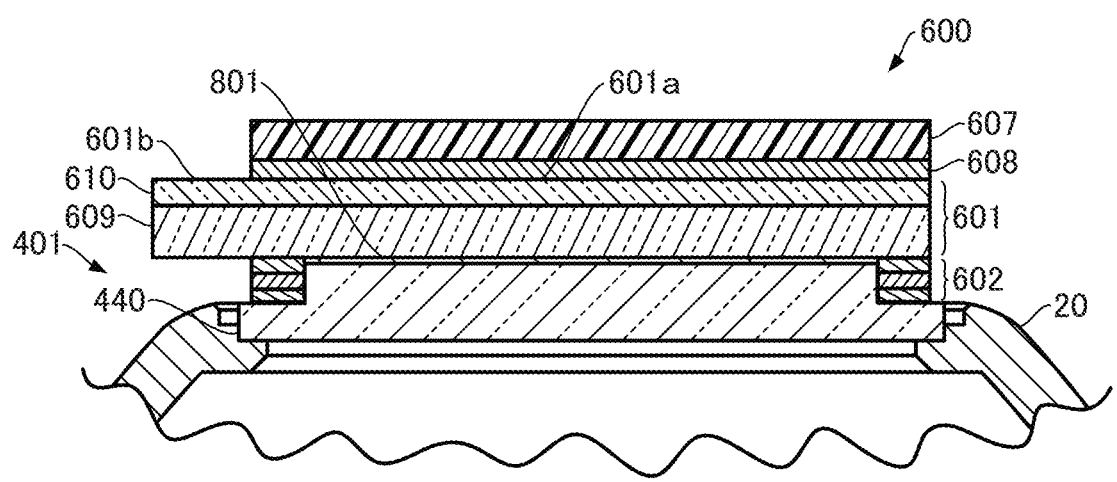
FIG. 21B is a schematic view illustrating how the imaging device cover according to Embodiment 8 of the present disclosure is attached to the imaging device in order of steps.

Subsequently, as illustrated in FIG. 20, steps S11 to S17 illustrated in FIG. 9 are sequentially performed. That is, the base sheet 606 is peeled off from the imaging device cover 600 (step S11), and the power button 5 of the imaging device 1 is turned on (step S12). Subsequently, in order to attach the imaging device cover 600 to the normal attachment position, the imaging device cover 600 is positioned (step S13), and is attached to the object cover 440 (step S14). In such a case, the imaging device cover 600 is attached while pushing out excess optical liquid material 801, and the pushed-out optical liquid material is wiped off. When the imaging device cover 600 is attached to the object cover 440 in this way, the optical liquid material 801 applied to the object cover 440 enters and fills a gap surrounded by the object cover 440, the cover member 601, and the double-sided tape 602 as illustrated in FIG. 21B.

Figure 21C:
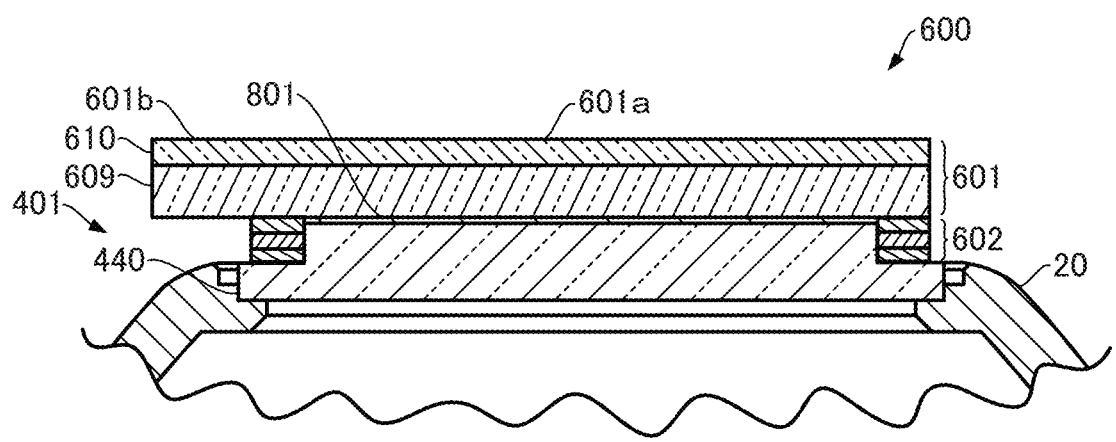
FIG. 21C is a schematic view illustrating how the imaging device cover according to Embodiment 8 of the present disclosure is attached to the imaging device in order of steps.

Subsequently, the protective member 607 is peeled off from the cover member 601 (step S15). Thus, as illustrated in FIG. 21C, the attachment of the imaging device cover 600 can be completed in the state in which the optical liquid material 801 is interposed without forming an air layer between the object cover 440 and the cover member 601.

Subsequently, imaging of a skin disease area is performed (step S16), and when imaging of all the skin disease areas of one patient are terminated, the imaging device cover 600 is removed from the imaging device 1 (step S17). Finally, the optical liquid material 801 remaining on the object cover 440 is wiped off (step S18), thereby terminating the imaging by the imaging device 1.

Note that an optical liquid material is not limited to the one made of epoxy and can be arbitrarily selected from high light-transmissive materials having a refractive index close to the refractive index (1.584) of a first layer, and may be made of, for example, acrylic.

According to the above embodiment, the gap between the object cover 440 and the cover member 601 is filled with the optical liquid material 801 having a refractive index close to the refractive index of the first layer 609. Thus, the difference between the refractive index of the first layer 609 and the refractive index of a member (that is, the optical liquid material 801) adjacent to the first layer 609 is reduced, which makes it possible to minimize reflection of light on the surface of the first layer 609. Therefore, the quality of a captured image can be improved.

Furthermore, since the optical liquid material 801 is filled between the object cover 440 and the cover member 601 and no air layer is formed, the occurrence of light interference fringes can be suppressed, which makes it possible to suppress degradation in the quality of a captured image.

The present disclosure is not limited to the above embodiments, and various modifications and applications are possible. In the above embodiments, in an image captured and stored in the memory card 13 (FIG. 2) and an image projected on the liquid crystal monitor 6 as a viewfinder, for example, as illustrated in FIGS. 8A and 8B, the colored layer 103, the support 20, and the like, which are located in a region outside the capturing assurance region R2, are also projected as they are. However, when an imaging device cover is attached to a position shifted from the normal position, the colored layer 103 is also shifted and projected, and a captured image tends to give a sense of discomfort. In order not to give such a sense of discomfort, an image may be processed so that objects projected outside the capturing assurance region R2 are not recognizable.

Figure 22A:
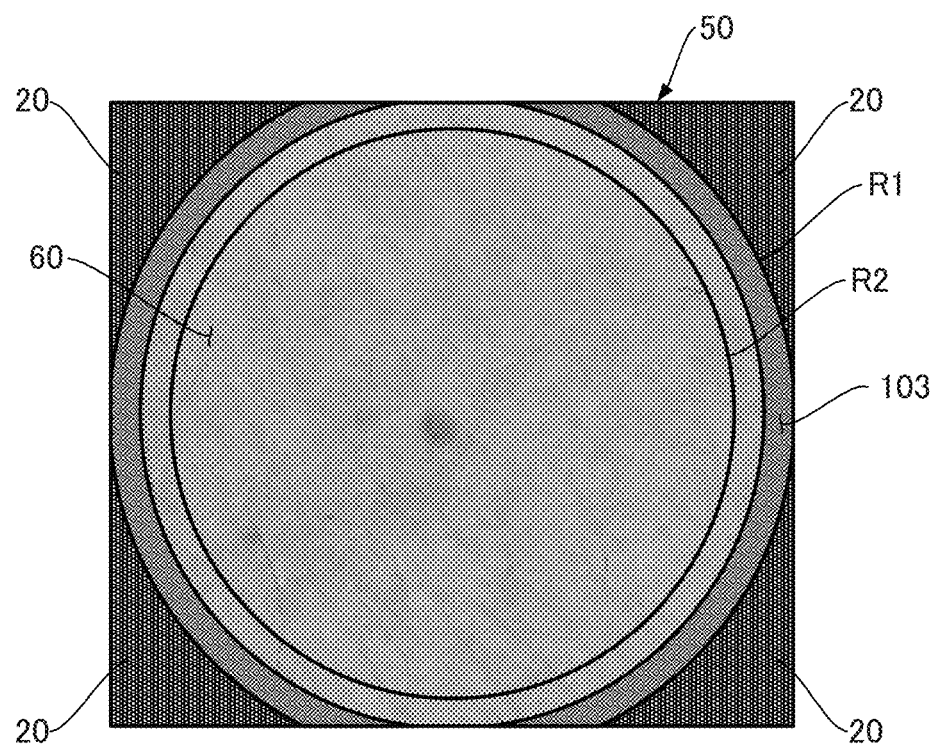
FIG. 22A is a diagram illustrating the image processing of the imaging device according to an embodiment of the present disclosure, and is a diagram illustrating an image before the processing.
Figure 22B:
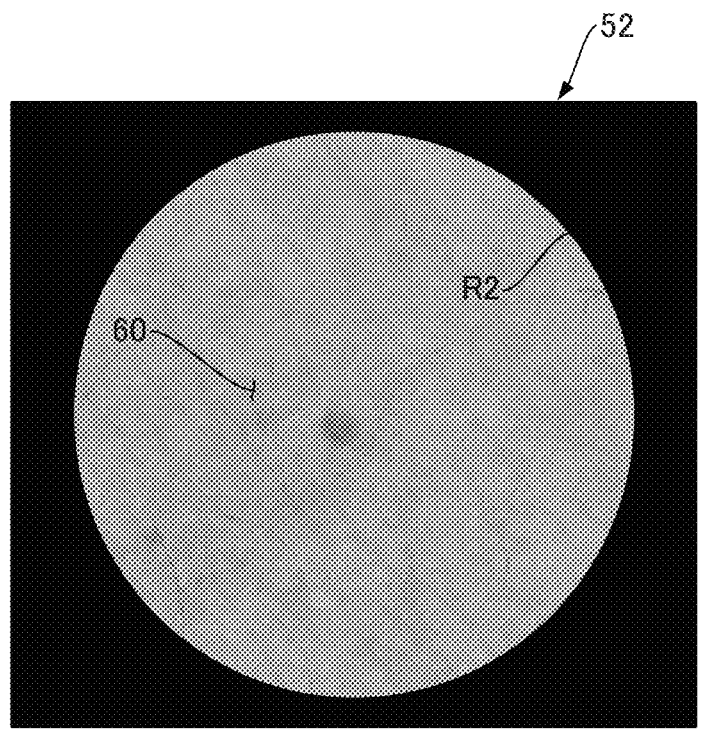
FIG. 22B is a diagram illustrating the image processing of the imaging device cover according to an embodiment of the present disclosure, and is a diagram illustrating an image after the processing.

For example, as illustrated in FIG. 22A, in an image 50 in which the colored layer 103 and the like appear outside the capturing assurance region R2, the image processing processor 11 (FIG. 2) may perform a process of painting the region outside the capturing assurance region R2 with a single color. FIG. 22B illustrates an image in which the outside of the capturing assurance region R2 is painted with black. When the image processing processor 11 performs such a process, the outside of the capturing assurance region R2 becomes unnoticeable, and an image of a skin 60 projected inside the capturing assurance region R2 can receive attention. Thus, an image that does not give a sense of discomfort can be generated. The image subjected to such processing may be stored in the memory card 13 (FIG. 2) or the like as a captured image, or may be adopted as an image to be projected on the liquid crystal monitor 6 as a viewfinder after an imaging device cover is attached.

Figure 23A:
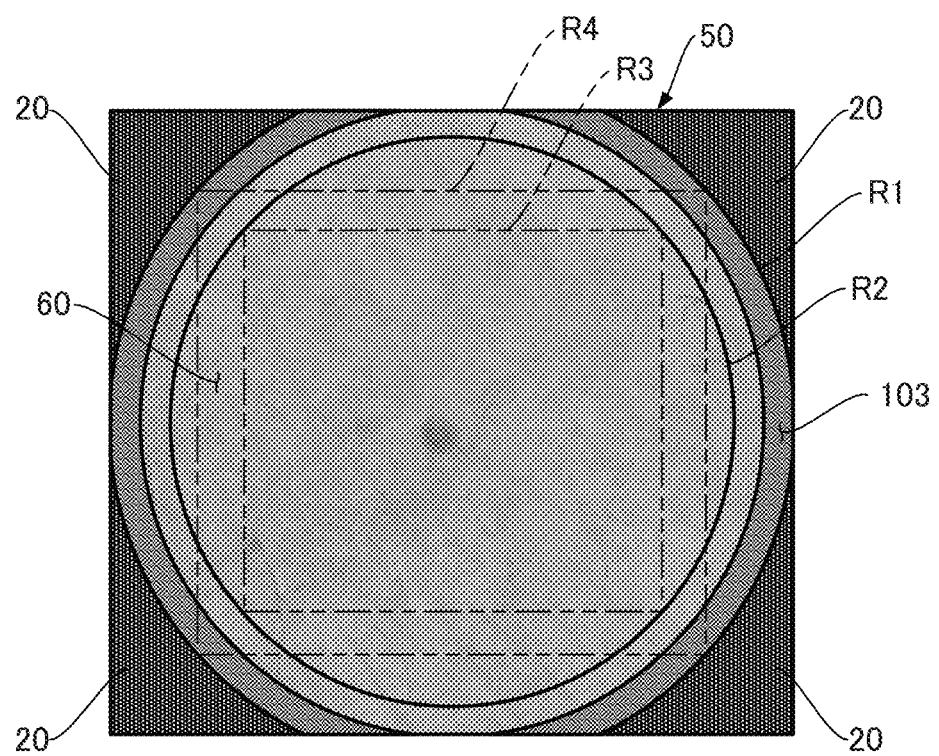
FIG. 23A is a diagram illustrating another image processing of the imaging device cover according to an embodiment of the present disclosure, and is a diagram illustrating an image before the processing.
Figure 23B:
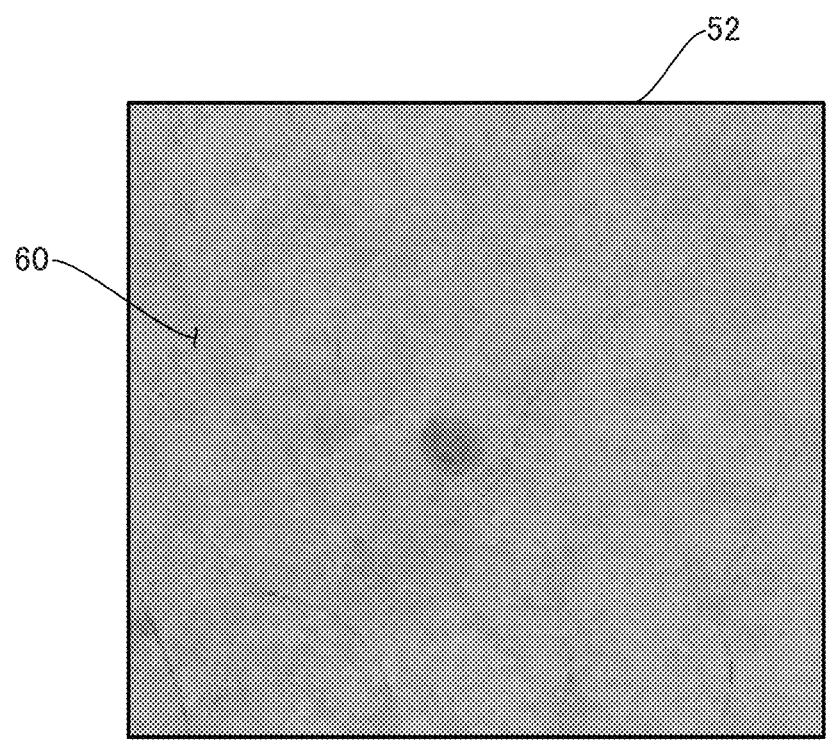
FIG. 23B is a diagram illustrating another image processing of the imaging device cover according to an embodiment of the present disclosure, and is a diagram illustrating an image after the processing.

As another image processing method, as illustrated in FIG. 23A, in an image 50 in which the colored layer 103 and the like appear outside the capturing assurance region R2, only an image within the capturing assurance region R2 may be cut out. A region R3 to be cut in this way is set to have, for example, a diagonal angle of view matching the capturing assurance region R2, and is cut out by digital zooming to generate an image 52 illustrated in FIG. 23B. Thus, as illustrated in FIG. 23B, the image 52 showing only the skin 60 can be generated. By performing such processing, the image 52 that is less likely to cause a sense of discomfort to an object person can be generated. The image subjected to such processing may be stored in the memory card 13 (FIG. 2) and/or the like as a captured image, or may be adopted as an image to be projected on the liquid crystal monitor 6 as a viewfinder after an imaging device cover is attached.

As another image processing method, as illustrated in FIG. 23A, a region R4 may be set to have, for example, a diagonal angle of view matching the capturable region R1, and may be cut out by digital zooming. Thus, since the support 20 not subjected to imaging is not projected in an image, an image that is less likely to cause a sense of discomfort can be generated. Furthermore, since the colored layer 103 can be projected in a small size at the four corners of the image, the imaging device cover 100 can be positioned while viewing an image projected on the liquid crystal monitor 6. Furthermore, since the colored layer 103 is only projected in a small size at the four corners of the image, there is no sense of discomfort in the image due to the colored layer 103 being projected.

In the above description, the liquid crystal monitor 6, which displays images as a viewfinder, displays a circle indicating the capturing assurance region R2 to support an imaging target so that the imaging target is captured within the capturing assurance region R2; however, whether to display the capturing assurance region R2 on the liquid crystal monitor 6 is arbitrary. The visibility of an image displayed on the liquid crystal monitor 6 can be improved by not displaying the capturing assurance region R2. Alternatively, an object person may select whether to display the capturing assurance region R2 by operating the touch panel of the liquid crystal monitor 6.

Although colors of a colored layer formed on the imaging device cover 100 have been described using red and black as an example, the colors of the colored layers are arbitrary. That is, an easy-to-recognize color may be adopted to emphasize workability, or an inconspicuous color may be adopted to emphasize the appearance of a captured image. In order to facilitate such determination, the imaging device cover 100 including colored layers of different colors is prepared in advance so that the color of the colored layer of the imaging device cover 100 used by an object person can be selected.

Furthermore, a material used for each adhesive layer is not limited to the above material, and can be arbitrarily selected as long as the function can be satisfied. For example, since the third adhesive layer 108 that peelably attaches the protective member 107 is attached to the cover member 101 that comes into contact with a skin at the time of imaging, the material is preferably a material that does not leave an adhesive residue, and a biocompatible adhesive.

In the above description, the protective member 107 is made of polyethylene; however, the protective member 107 may be made of any material that can protect the cover member 101 because the protective member 107 is removed at the time of imaging. For example, the protective member 107 may be made of polyethylene terephthalate or polypropylene. Furthermore, the protective member 107 has been described as being pale green; however, the color of the protective member can be arbitrarily selected as long as the protective member 107 is colored with high-brightness color so that the protective member 107 is displayed brightly on a liquid crystal monitor even when the background is dark when an imaging device cover is attached.

Furthermore, since the cover member 101 is used as an optical transmission surface, the cover member 101 is preferably made of a material that does not easily wrinkle. In the above embodiment, the cover member 101 is made of a sheet material; however, the cover member 101 may be made of a plate material having a higher bending rigidity. In order not to affect the polarization performance of an imaging device, the cover member 101 is preferably selected from materials having a low birefringence, flat spectral transmittance with little change in color, and biocompatibility. Moreover, the cover member 101 (region of the peripheral portion 101*a* other than the colored layer 103) is preferably selected from materials that transmit light in the convertible wavelength region of the imaging element 8 described above. For example, the cover member 101 is preferably made of polycarbonate, acrylic, or triacetyl cellulose in addition to polycarbonate.

Furthermore, a colored layer provided on the peripheral portion of the cover member 101 needs not to be formed in an annular continuous shape, and may be intermittently formed on the peripheral portion of the cover member 101. For example, even when the colored layer is intermittently formed, the colored layer needs to be formed on the peripheral portion of the cover member 101 to such an extent that position displacement can be intuitively recognized when the imaging device cover 100 is positioned.

In the above embodiment, the first adhesive layer 104 for attaching the cover member 101 to the object cover 40 and the colored layer 103 colored for easy identification in an image are separately configured; however, the first adhesive layer 104 itself may be colored to serve as the colored layer 103. That is, this configuration includes a case in which the first adhesive layer 104 includes the colored layer 103 and a case in which the first adhesive layer 104 does not include the colored layer 103.

In the above description, the cover member 101 and the colored layer 103 are separately configured; however, for example, the peripheral portion of the cover member 101 may be colored so that the cover member 101 serve as the colored layer 103. That is, this configuration includes a case in which the cover member 101 includes a colored layer and a case in which the cover member 101 includes no colored layer. For example, when the peripheral portion of the cover member 101 includes a black colored layer, the peripheral portion transmits no light. In such a case, the cover member 101 transmits light in a partial region except for the peripheral portion.

In the case of an imaging device that visualizes light of a specific wavelength, such as an infrared camera or an ultraviolet camera, the cover member 101 may be made of a material that transmits the wavelength, may not need to be made of a transparent sheet material, and may be made of a translucent material.

In the above description, the protection member 107 includes no portion corresponding to the protruding portion 101*b* of the cover member 101 and the protection member 107 and the cover member 101 are not of the same shape; however, the protection member 107 may be provided with a portion corresponding to the protruding portion 101*b* and the protective member 107 and the cover member 101 may have the same shape. When the protective member 107 and the cover member 101 are formed to have the same shape, the step difference h illustrated in FIG. 7B does not occur, thereby preventing the occurrence of the problem that the cover member 101 is unintentionally peeled off from the step difference h.

In the imaging device cover 600 illustrated in FIG. 16, the cover member 601 has been described as having a stacked structure of a layer made of polycarbonate and a layer made of acrylic resin; however, materials constituting the stacked structure are not limited to these materials. By appropriately combining materials with different physical properties, cover members having various properties can be achieved. Furthermore, the thickness of each of the two layers can be arbitrarily set. Moreover, a cover member may be a stacked body of two or more layers.

In Embodiment 8, the method of applying an optical liquid material to an object cover and attaching the imaging device cover 600 according to Embodiment 6 to the imaging device 401 of Embodiment 4 has been described; however, this method can also be adopted when attaching other imaging device covers. For example, the method can be applied to the imaging device covers 300 (FIG. 11) and 500 (FIG. 14) according to Embodiment 3 and Embodiment 5 in which an object cover and a cover member can be brought into contact with each other or the gap between the object cover and the cover member can be reduced. Furthermore, the method can be applied to the imaging device covers 100 (FIG. 6) and 200 (FIG. 10) of Embodiment 1 and Embodiment 2 in which a gap is formed between an object cover and a cover member. Thus, an air layer between the object cover and the cover member can be further removed. When the cover member includes a single layer, an optical liquid material is preferably selected from materials having a refractive index close to the refractive index of the cover member. Thus, the reflection of light on the surface of the cover member can be minimized, and the quality of a captured image can be improved.

Furthermore, the number of adhesive covers to be installed on one base sheet is arbitrary, and may be 1 or 6 or less as described above. On the other hand, the number of adhesive covers is preferably limited within a range that allows easy handling of the base sheet.

Furthermore, an imaging device is not limited to a dermoscopy camera, and various imaging devices can be used. For example, examples of various imaging devices include imaging devices that capture the surfaces of animals and plants, security cameras, imaging devices that capture underwater, imaging devices used in outer space, imaging devices used to inspect concrete and steel structures such as buildings and bridges, or imaging devices used underground or in an underground space. In these imaging devices, when an object cover is dirty, the present disclosure can be applied when an object cover is desired to be maintained in a sanitary condition. Furthermore, the imaging device includes not only a device for imaging still images but also a device for capturing moving images.

The present disclosure can also be applied to imaging devices attached to other devices, such as imaging devices installed in computers, televisions, game machines, smartphones, and tablet terminals.

Furthermore, the object cover 40 is not limited to a circular shape, and may have a polygonal shape such as a quadrangle, a triangle, or a pentagon. Similarly, the shape of the imaging device cover 100 that covers the object cover 40 is not limited to a circular shape. Furthermore, the object cover 40 and the imaging device cover 100 may not have the same shape, and one may be circular and the other may be polygonal.

The foregoing describes some example embodiments for explanatory purposes. Although the foregoing discussion has presented specific embodiments, persons skilled in the art will recognize that changes may be made in form and detail without departing from the broader spirit and scope of the disclosure. Accordingly, the specification and drawings are to be regarded in an illustrative rather than a restrictive sense. This detailed description, therefore, is not to be taken in a limiting sense, and the scope of the disclosure is defined only by the included claims, along with the full range of equivalents to which such claims are entitled.

This application claims the benefit of Japanese Patent Application No. 2020-149989, filed on Sep. 7, 2020, and Japanese Patent Application No. 2021-010405, filed on Jan. 26, 2021, of which the entirely of the disclosure is incorporated by reference herein.

INDUSTRIAL APPLICABILITY

The present disclosure is particularly useful in capturing an appropriate image while taking into consideration the sanitation of an imaging device.

REFERENCE SIGNS LIST

1 Imaging device
2 Controller
3 Camera body
3*a* Light exit hole
4 Shutter button
5 Power button
6 Liquid crystal monitor
7 Imaging lens system
8 Imaging element
10 Cover structure
11 Image processing processor
12 Internal memory
13 Memory card
20 Support
20*a* Screw
21 Opening
40 Object cover
50 Image
52 Image
60 Skin
100 Imaging device cover
101 Cover member
101*a* Circular portion
101*b* Protruding portion
101*c* Cover peripheral portion
102 Double-sided tape
103 Colored layer
103*a* Inner edge
104 First adhesive layer
105 Second adhesive layer
106 Base sheet
107 Protective member
108 Third adhesive layer
109 Outer edge
110 Outer edge
200 Imaging device cover
203 Colored layer
204 First adhesive layer
300 Imaging device cover
301 Cover member
301*a* Circular portion
301*b* Protruding portion
301*c* Accommodator
401 Imaging device
440 Object cover
440*a* Accommodator
500 Imaging device cover
501 Cover member
502 Double-sided tape
504 First adhesive layer
507 Protective member
510 Cover structure
510*a* Male thread
520 Support
550 Attachment
550*a* Female thread
550*b* Attachment surface portion
550*c* Upright portion
600 Imaging device cover
601 Cover member
601*a* Circular portion
601*b* Protruding portion
602 Double-sided tape
603 Colored layer
604 First adhesive layer
605 Second adhesive layer
606 Base sheet
607 Protective member
608 Third adhesive layer
609 First layer 610 Second layer
611 Adhesive cover
700 Imaging device cover
706 Base sheet
801 Optical liquid material
1000 Imaging device cover
1001 Cover member
1003 Push-pull gauge
1004 Pressing portion
D1 Inner diameter
D2 Diameter
d1, d2, d3 Depth
h Step difference
O, O' Center
R1 Capturable region
R2 Capturing assurance region
R3, R4 Region
S Gap
W1, W2, W3, W4 Width
W5 Amount of protrusion

The invention claimed is:

1. An imaging device cover comprising:
a cover member comprising a partial region that transmits incident light and a cover peripheral portion;
a first adhesive layer provided on the cover peripheral portion of the cover member,
wherein, while covering an object cover that guides reflected light from a target to a lens of an imaging device including the object cover, the cover member is peelably attached to the imaging device via the first adhesive layer; and
a colored layer,
wherein the cover member, the colored layer and the first adhesive layer are stacked in this order in a thickness direction of the cover member, and
wherein in a state where:
(i) the cover member is peelably attached to the imaging device by the first adhesive layer to transmit the incident light through the partial region of the cover member and an opening of a cover structure of the imaging device to be captured by the imaging device as an image, and
(ii) a center of an at least partially annular shape in the image corresponding to an opening of the colored layer matches a center of a capturable region in the image corresponding to the opening of the cover structure,
the colored layer is provided relative to the cover member such that at least a portion of the colored layer protrudes inward from an outer edge of the capturable region of the image.

2. The imaging device cover according to claim 1, wherein the colored layer is printed in an annular shape on the cover peripheral portion.

3. The imaging device cover according to claim 1, further comprising:
a second adhesive layer to attach the colored layer to the cover peripheral portion,
wherein the second adhesive layer, the colored layer, and the first adhesive layer are stacked on the cover peripheral portion in this order from the cover peripheral portion in the thickness direction of the cover member.

4. The imaging device cover according to claim 3, wherein an adhesive strength of the second adhesive layer is higher than an adhesive strength of the first adhesive layer.

5. The imaging device cover according to claim 3, wherein the second adhesive layer, the colored layer, and the first adhesive layer form a double-sided tape using the colored layer as a base material, and
wherein the double-sided tape is formed in an annular shape on the cover peripheral portion.

6. The imaging device cover according to claim 1, wherein the cover member comprises a protruding portion that is held by an object person when attaching or detaching the imaging device cover and protrudes outward from an outer edge of the cover peripheral portion.

7. The imaging device cover according to claim 1, wherein the cover member is made of a sheet material.

8. The imaging device cover according to claim 1, wherein the cover member comprises a stacked body in which at least a first layer and a second layer are integrated, the first layer and the second layer being made of different materials.

9. The imaging device cover according to claim 8, wherein the second layer is made of a material having a higher bending rigidity than the first layer, and
wherein the first layer is disposed closer to a side of the first adhesive layer than the second layer.

10. The imaging device cover according to claim 8, wherein the first layer is made of polycarbonate, and
wherein the second layer is made of acrylic resin.

11. The imaging device cover according to claim 1, wherein, when the imaging device is used to capture an image with the object cover in contact with a diseased area, the cover member has a bending rigidity that prevents the cover member from coming into contact with the object cover.

12. The imaging device cover according to claim 1, further comprising:
a protective member to cover and protect the cover member until the imaging device is used, the protective member being peeled off from the cover member at the time of imaging by the imaging device and being made of a material having lower light transmission than the cover member;
a third adhesive layer to peelably attach the protective member to a surface of the cover member opposite to a side of the first adhesive layer; and
a base sheet peelably attached to the first adhesive layer and peeled off from the first adhesive layer when attached to the imaging device.

13. The imaging device cover according to claim 12, wherein the protective member is colored.

14. The imaging device cover according to claim 1, wherein the cover peripheral portion is formed at a position recessed on an opposite side of the object cover from a portion of the cover member other than the cover peripheral portion.

15. A system comprising:
the imaging device cover according to claim 1; and
the imaging device,
wherein the imaging device is configured to capture an image to support diagnosis of a diseased area in a first imaging state that is a normal imaging state and a second imaging state in which the object cover is brought closer to the diseased area and imaging of the diseased area is performed, and
wherein the cover member is configured to be peelably attached to the object cover via the first adhesive layer.

16. A system comprising:
the imaging device cover according to claim 1; and
the imaging device, wherein the imaging device is configured to capture an image to support diagnosis of a diseased area in a first imaging state that is a normal imaging state and a second imaging state in which the object cover is brought closer to the diseased area, and wherein the first adhesive layer is configured to be attached to a portion of the imaging device outside the object cover, and the portion attached with the first adhesive layer is formed at a position recessed toward a side of the lens from the object cover.

17. The system according to claim 16, further comprising:
an attachment configured to be detachably attached to the portion of the imaging device outside the object cover, wherein the imaging device cover is configured to be peelably attached to the attachment.

18. A system comprising:
the imaging device cover according to claim 1; and
the imaging device,
wherein the imaging device is configured to support diagnosis of a diseased area in a first imaging state that is a normal imaging state and a second imaging state in which the object cover is brought closer to the diseased area, and
wherein the imaging device cover is configured to be peelably attached to the object cover via the first adhesive layer in a normal attachment position such that in an image captured through the object cover, an image of the colored layer is captured outside a capturing assurance region set at a center of the captured image.

19. The system according to claim 18, wherein the imaging device is configured to generate an image by painting a region outside the capturing assurance region in the captured image with a single color.

20. The system according to claim 18, wherein the imaging device is configured to cut out an image with a diagonal angle of view matching the capturing assurance region from the captured image.

21. A method comprising:
attaching the imaging device cover according to claim 1 to the object cover via the first adhesive layer;
bringing the object cover close to a diseased area and operating the imaging device to perform dermoscopy imaging in a state in which the imaging device cover is attached; and
removing the imaging device cover from the object cover after the dermoscopy imaging is terminated.

22. A method comprising:
applying an optical liquid material having light transmission to an inside of a region of the object cover of the imaging device to which the first adhesive layer of the imaging device cover according to claim 1 is attached, and attaching the imaging device cover to the object cover via the first adhesive layer;
bringing the object cover close to a diseased area and operating the imaging device to perform dermoscopy imaging in a state in which the imaging device cover is attached; and
removing the imaging device cover from the object cover after the dermoscopy imaging is terminated.

23. The method according to claim 22, wherein the optical liquid material has a refractive index close to a refractive index of an adjacent cover member.

24. A method comprising:
attaching the imaging device cover according to claim 1 to the object cover via the first adhesive layer;
bringing the object cover close to a diseased area and performing dermoscopy imaging in a state in which the imaging device cover is attached; and
removing the imaging device cover from the object cover after the dermoscopy imaging is terminated,
wherein when the colored layer is provided relative to the cover member such that the at least a portion of the colored layer protrudes inward from the outer edge of the capturable region of the image, the imaging device cover is positioned so that the colored layer captured in the image is located outside a capturing assurance region set at a center of the image.

* * * * *